US006033903A

United States Patent [19]

Sisk et al.

[11] Patent Number: 6,033,903

[45] Date of Patent: Mar. 7, 2000

[54] METHOD OF EXPRESSING AND SECRETING SOLUBLE EXTRACELLULAR DOMAINS OF HUMAN GONADOTROPIN HORMONE RECEPTORS

[75] Inventors: William P. Sisk, Boxborough; Shirley Vui Yen Cheng, Wellesley; David Rogers Buckler, Wayland; Holly Lynn Prentice, Acton, all of Mass.

[73] Assignee: Applied Research Systems, Ars Holding N.V., Curacao, Netherlands Antilles

[21] Appl. No.: 08/460,576

[22] Filed: Jun. 2, 1995

[51] Int. Cl.[7] .................................................... C12N 15/00

[52] U.S. Cl. .................... 435/320.1; 435/69.4; 435/69.1; 435/69.7; 435/69.8; 435/325; 435/348; 435/455; 435/456; 530/398; 530/397; 536/23.51

[58] Field of Search ................................ 435/69.1, 69.4, 435/69.7, 69.8, 240.2, 252.3, 172.3, 320.1, 325, 348, 455, 456; 530/413, 350, 398, 397; 536/23.51

[56] References Cited

U.S. PATENT DOCUMENTS

| | | | |
|---|---|---|---|
| 5,023,328 | 6/1991 | Summers et al. . | |
| 5,155,037 | 10/1992 | Summers | 435/240.2 |
| 5,278,050 | 1/1994 | Summers . | |
| 5,516,657 | 5/1996 | Murphy et al. | 435/69.3 |

FOREIGN PATENT DOCUMENTS

| | | |
|---|---|---|
| 0 614 975 A1 | 9/1994 | European Pat. Off. . |
| 614 975 A1 | 9/1994 | European Pat. Off. . |
| 90 05783 | 5/1990 | WIPO . |

OTHER PUBLICATIONS

Cristophe, Sylvie et al., "Expression of the Human Follicle–Stimulating Hormone Receptor in the Baculovirus System." Biochemical and Biophysical Research Communications vol. 196, No. 1, pp. 402–408 (1993).

Tilly, Jonathan et al., "Expression of Recombinant Human Follicle–Stimulating Hormone Receptor: Species–Specific Ligand Building, Signal Transduction, and Identification of Multiple Ovarian Messenger Ribonucleic Acid Transcripts." Endocrinology vol. 131, No. 2, pp. 799–806 (1992).

Klausner, Richard et al., "Protein Degradation in the Endoplasmic Reticulum." Cell vol. 62, pp. 611–614 (1990).

Huang, G.C. et al., "The thyrotrophin hormone receptor of Grave's disease: overexpression of the extracellular domain in insect cells using recombinant baculovirus, immunoaffinity purification and analysis of autoantibody binding." Journal of Medical Endocrinology, vol. 10, pp. 127–142 (1993).

Seetharamaiah, G.S. et al., "Induction of TSH Binding Inhibitory Immunoglobulins with the Extracellular Domain of Human Thyrotropin Receptor Produced using Baculovirus Expression System." Autoimmunity vol. 14 pp. 315–320 (1993).

Seetharamaih, G.S. et al., "A recombinant extracellular domain of the Tyrotropin (TSH) receptor binds TSH the absence of membranes." Endocrinology vol. 134, No. 2, pp. 549–554 (1994).

Society for the Study of Reproduction Supplement No. 1, Biology of Reproduction, vol. 46, #330. Tilly, J. et al., "Biochemical and functional analysis of recombinant human follicle–stimulating hormone (FSH) receptor."

Xunxian, Liu et al., "Accessibility of rat and human follitropin receptor primary sequence (R265–S296) in situ." Endocrinology vol. 135, No. 2, pp. 682–691 (1994).

Wenyong, Chen et al., "High expression of the hormone binding active extracellular domain (1–294) of rat lutropin receptor in *Escherichia coli*." Molecular and Cellular Endocrinology vol. 91, pp. 35–41 (1993).

Bernard, M.P. et al., "Cloning of rast lupotropin (LH) receptor analogs lacking the soybean lectin domain." Molecular and Cellular Endocrinology vol. 71, pp. R19–R23 (1990).

Davis, David et al., "Identification of the sites of N–linked glycosylation on the follicle–stimulating hormone (FSH) receptor and assessment of their role in FSH receptor function." Molecular Endocrinology vol. 9, pp. 159–170 (1995).

Wimalasena, Jayantha et al., "Soluble luteinizing hormone/human chorionic gonadotropin receptors of the rat ovary: Comparative studies of water– and detergent–soluble receptors." Endocrinology vol. 113, No. 2, pp. 618–624 (1983).

Ji, Inhae et al., "Exons 1–10 of the rat LH receptor encode a high affinity hormone binding site and exon 11 encodes G–Protein modulation and a potential second hormone binding site." Endocrinology vol. 128, No. 5, pp. 2648–2650 (1991).

Moyle, William et al., "Leutropin/B–Adrenergic receptor chimeras bind choriogonadotropin and adrenergic ligands but are not expressed at the cell surface." The Journal of Biological Chemistry vol. 266, No. 17 pp. 10807–10812 (1991).

Kelton, Christie et al., "The cloning of the human follicle stimulating hormone receptor and its expression in COS–7, CHO, and Y–1 cells." Molecular and Cellular Endocrinology vol. 89, pp. 141–151 (1992).

(List continued on next page.)

*Primary Examiner*—Paula K. Hutzell
*Assistant Examiner*—Eliane Lazar-Wesley
*Attorney, Agent, or Firm*—Browdy and Neimark

[57] ABSTRACT

The extracellular domain, or fragment thereof, of a gonadotropin glycoprotein hormone receptor is expressed and secreted in a soluble and functionally hormone-binding form. A recombinant baculovirus transfer vector is constructed to include a gene segment encoding the extracellular domain, or fragment thereof, of the glycoprotein hormone receptor joined in frame with a gene segment encoding a baculovirus signal peptide and operably linked to a baculovirus promoter. Recombinant baculovirus generated by transfection or co-transfection of insect cells are then used to infect insect host cells for the expression and secretion of soluble receptor.

14 Claims, 9 Drawing Sheets

OTHER PUBLICATIONS

Yan–Bo, Xie et al., "Extracellular domain of lupotropin/chrioiogonadtropin receptor expressed in transfected cells binds choriogonadotropin with high affinity." The Journal of Biological Chemistry vol. 265, No. 35, pp. 21411–21414 (1990).

Chon, Hwa, Tsai–Morris et al., "Intronic nature of the rat luteinizing hormone receptor gene defines a soluble receptor subspecies with hormone binding activity." The Journal of Biological Chemistry vol. 265, No. 32. pp. 19385–19388 (1990).

Pajot–Augy, P. et al., "High–level expression on recombinant porcine LH receptor in baculovirus–infected insect cells or caterpillars." Journal of Molecular Endocrinology vol. 14, pp. 51–66 (1995).

Sisk, William et al., "High–level expression and purification of secreted forms of herpes simplex virus type 1 glycoprotein gD synthesized by baculovirus–infected insect cells." Journal of Virology vol. 68, No. 2, pp. 766–775 (1994).

Tessier, Daniel et al., "Enhanced secretion from insect cells of a foreign protein fused to the honeybee melittin signal peptide." Gene vol. 98, pp. 177–183 (1991).

Murphy, Cheryl et al., "Enhanced expression, secretion, and large–scale purification of recombinant HIV–1 gp120 in insect cells using the baculovirus egt and p67 signal peptides." Protein Expression and Purification vol. 4, pp. 349–357 (1993).

Vlase et al., Endocrinology 138:1658–1666, 1997.

Gattadahalli et al., J.Immunol.22:2798–2804, 1997.

Jarvis et al., J.Biol.Chem. 268:16754–16762, 1993.

Invitrogen product catalog, p. 20, 1996.

GIBCO BRL, Product Catalogue and reference guide 1995–96, p. 18–32.

Luckow et al, Bio/technolgy 6: 47–55, 1988.

Minegishi, Biochem.Biophys.Res.Com. 175(3):1125–1130, 1991.

Minegishi, Biochem.Biophys.Res.Com. 172(3):1049–1054, 1990.

CHO.366
CHO.366.NS
CPM BOUND
30000
25000
20000
15000
10000
5000
0
0.001
0.01
0.1
1
DILUTION FACTOR OF FSHR-EC

PacI (579)
NdeI (9546)
XcmI (739)
SacII (868)
BstEII (923)
ApaI (1395)
XhoI (1901)
SphI (2131)
BclI (2232)
ScaI (8854)
GsuI (8461)
AlwNI (7894)
R Amp
ori
pAcGP67 A
9.7 kbp
unique sites underlined
polyhedrin promoter
gp67 leader sequence
NaeI (3770)
EcoRV (3998)
SpeI (4140)
SnaBI (4938)
PpuMI (4308)
MCS
Pst I
Bcl I
ScaI (9875)
R Amp
ori
BclI (2232)
pAcgp67-FSHR-EC
10.782 bp
FSHR-EC
promoter (3998)
gp67 so (4135)
Bam'/BcI' (4251)
PstI
polyA

FIG. 3A

```
    polyhedrin promoter
  1 GATATCATGGAGATAATTAAAATGATAACCATCTCGCAAATAAATAAGTATTTTACTGTTTTCGTAACAGTTTTGTAATAAAAAAACCT

          polyhedrin'                                              gp67 signal peptide
 90 ATAAAT ATT CCG GAT TAT TCA TAC CGT CCC ACC ATC GGG CGC GGA TCT ATG CTA CTA GTA AAT
                                                            1► Met Leu Leu Val Asn

153 CAG TCA CAC CAA GGC TTC AAT AAG GAA CAC ACA AGC AAG ATG GTA AGC GCT ATT GTT
 6► Gln Ser His Gln Gly Phe Asn Lys Glu His Thr Ser Lys Met Val Ser Ala Ile Val
                                                            |
210 TTA TAT GTG CTT TTG GCG GCG GCG GCG CAT TCT GCC TTT GCG ▼
25► Leu Tyr Val Leu Leu Ala Ala Ala Ala His Ser Ala Phe Ala

  BamHi'/BcII' -1 mature FSHR (putative)
252 GCG GAT CAG TGT CAT CAT CGG ATC TGT CAC TGC TCT AAC AGG GTT TTT CTC TGC CAA GAG AGC AAG
39► Ala Asp Gln Cys His His Arg Ile Cys His Cys Ser Asn Arg Val Phe Leu Cys Gln Glu Ser Lys

318 GTG ACA GAG ATT CCT TCT GAC CTC CCG AGG AAT GCC ATT GAA CTG AGG TTT GTC CTC ACC AAG CTT
61► Val Thr Glu Ile Pro Ser Asp Leu Pro Arg Asn Ala Ile Glu Leu Arg Phe Val Leu Thr Lys Leu

384 CGA GTC ATC CAA AAA GGT GCA TTT TCA GGA TTT GGG GAC CTG GAG AAA ATA GAG ATC TCT CAG AAT
83► Arg Val Ile Gln Lys Gly Ala Phe Ser Gly Phe Gly Asp Leu Glu Lys Ile Glu Ile Ser Gln Asn

450 GAT GTC TTG GAG GTG ATA GAG GCA GAT GTG TTC TCC AAC CTT CCC AAA TTA CAT GAA ATT AGA ATT
105► Asp Val Leu Glu Val Ile Glu Ala Asp Val Phe Ser Asn Leu Pro Lys Leu His Glu Ile Arg Ile

516 GAA AAG GCC AAC AAC CTG CTC TAC ATC AAC CCT GAG GCC TTC CAG AAC CTT CCC AAC CTT CAA TAT
127► Glu Lys Ala Asn Asn Leu Leu Tyr Ile Asn Pro Glu Ala Phe Gln Asn Leu Pro Asn Leu Gln Tyr

582 CTG TTA ATA TCC AAC ACA GGT ATT AAG CAC CTT CCA GAT GTT CAC AAG ATT CAT TCT CTC CAA AAA
149► Leu Leu Ile Ser Asn Thr Gly Ile Lys His Leu Pro Asp Val His Lys Ile His Ser Leu Gln Lys

648 GTT TTA CTT GAC ATT CAA GAT AAC ATA AAC ATC CAC ACA ATT GAA AGA AAT TCT TTC GTG GGG CTG
171► Val Leu Leu Asp Ile Gln Asp Asn Ile Asn Ile His Thr Ile Glu Arg Asn Ser Phe Val Gly Leu
```

FIG. 3B

```
 714   AGC TTT GAA AGT GTG ATT CTA TGG CTG AAT AAG AAT GGG ATT CAA GAA ATA CAC AAC TGT GCA TTC
 193 ►Ser Phe Glu Ser Val Ile Leu Trp Leu Asn Lys Asn Gly Ile Gln Glu Ile His Asn Cys Ala Phe

 780   AAT GGA ACC CAA CTA GAT GAG CTG AAT CTA AGC GAT AAT AAT AAT TTA GAA GAA TTG CCT AAT GAT
 215 ►Asn Gly Thr Gln Leu Asp Glu Leu Asn Leu Ser Asp Asn Asn Asn Leu Glu Glu Leu Pro Asn Asp

 846   GTT TTC CAC GGA GCC TCT GGA CCA GTC ATT CTA GAT ATT TCA AGA ACA AGG ATC CAT TCC CTG CCT
 237 ►Val Phe His Gly Ala Ser Gly Pro Val Ile Leu Asp Ile Ser Arg Thr Arg Ile His Ser Leu Pro

 912   AGC TAT GGC TTA GAA AAT CTT AAG AAG CTG AGG GCC AGG TCG ACT TAC AAC TTA AAA AAG CTG CCT
 259 ►Ser Tyr Gly Leu Glu Asn Leu Lys Lys Leu Arg Ala Arg Ser Thr Tyr Asn Leu Lys Lys Leu Pro

 978   ACT CTG GAA AAG CTT GTC GCC CTC ATG GAA GCC AGC CTC ACC TAT CCC AGC CAT TGC TGT GCC TTT
 281 ►Thr Leu Glu Lys Leu Val Ala Leu Met Glu Ala Ser Leu Thr Tyr Pro Ser His Cys Cys Ala Phe

1044   GCA AAC TGG AGA CGG CAA ATC TCT GAG CTT CAT CCA ATT TGC AAC AAA TCT ATT TTA AGG CAA GAA
 303 ►Ala Asn Trp Arg Arg Gln Ile Ser Glu Leu His Pro Ile Cys Asn Lys Ser Ile Leu Arg Gln Glu

1110   GTT GAT TAT ATG ACT CAG ACT AGG GGT CAG AGA TCC TCT CTG GCA GAA GAC AAT GAG TCC AGC TAC
 325 ►Val Asp Tyr Met Thr Gln Thr Arg Gly Gln Arg Ser Ser Leu Ala Glu Asp Asn Glu Ser Ser Tyr

1176   AGC AGA GGA TTT GAC ATG ACG TAC ACT GAG TTT GAC TAT GAC TTA TGC AAT GAA GTG GTT GAC GTG
 347 ►Ser Arg Gly Phe Asp Met Thr Tyr Thr Glu Phe Asp Tyr Asp Leu Cys Asn Glu Val Val Asp Val

1242   ACC TGC TCC CCT AAG CCA GAT GCA TTC AAC CCA TGT GAA GAT ATC ATG GGG TAC AAC ATC CTC AGA
 369 ►Thr Cys Ser Pro Lys Pro Asp Ala Phe Asn Pro Cys Glu Asp Ile Met Gly Tyr Asn Ile Leu Arg

        (1311) PstI
1308   TAG CTG CAG
 391 ► ...
```

CPM BOUND
30000
25000
20000
15000
10000
5000
0
0.001
0.01
0.1
1
DILUTION FACTOR OF FSHR-EC MEDIA
FSHEC
FNS

F/G. 5
BACULO FSHR-EC CPM BOUND
20000
16000
12000
8000
4000
0
Bac. FSHR. EC
CHO366
CHO-366 CPM BOUND
10000
8000
6000
4000
2000
[r-hFSH] M
1E-15
1E-14
1E-13
1E-12
1E-11
1E-10
1E-9
1E-8
1E-7
1E-6

FSHR.EC.1
FSHR.EC.2
CONTROL
SPECIFIC COUNTS (cpm)
8000
4000
0
0.00001
0.0001
0.001
0.01
0.1
DILUTION FACTOR F I G. 7
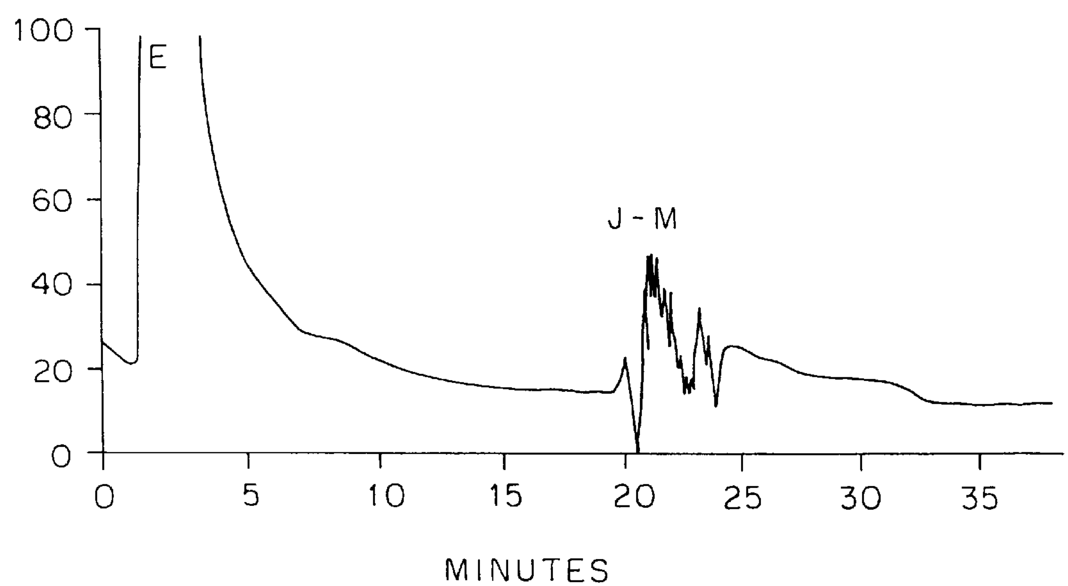

```
                               SEQUENCE LISTING


(1) GENERAL INFORMATION:

   (iii) NUMBER OF SEQUENCES: 18


(2) INFORMATION FOR SEQ ID NO:1:

     (i) SEQUENCE CHARACTERISTICS:
          (A) LENGTH: 1316 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 138..1307

    (xi) SEQUENCE DESCRIPTION: SEQ ID NO:1:

GATATCATGG AGATAATTAA AATGATAACC ATCTCGCAAA TAAATAAGTA TTTTACTGTT     60

TTCGTAACAG TTTTGTAATA AAAAAACCTA TAAATATTCC GGATTATTCA TACCGTCCCA    120

CCATCGGGCG CGGATCT ATG CTA CTA GTA AAT CAG TCA CAC CAA GGC TTC       170
                   Met Leu Leu Val Asn Gln Ser His Gln Gly Phe
                     1               5                  10

AAT AAG GAA CAC ACA AGC AAG ATG GTA AGC GCT ATT GTT TTA TAT GTG      218
Asn Lys Glu His Thr Ser Lys Met Val Ser Ala Ile Val Leu Tyr Val
             15                  20                  25

CTT TTG GCG GCG GCG GCG CAT TCT GCC TTT GCG GCG GAT CAG TGT CAT      266
Leu Leu Ala Ala Ala Ala His Ser Ala Phe Ala Ala Asp Gln Cys His
         30                  35                  40

CAT CGG ATC TGT CAC TGC TCT AAC AGG GTT TTT CTC TGC CAA GAG AGC      314
His Arg Ile Cys His Cys Ser Asn Arg Val Phe Leu Cys Gln Glu Ser
     45                  50                  55

AAG GTG ACA GAG ATT CCT TCT GAC CTC CCG AGG AAT GCC ATT GAA CTG      362
Lys Val Thr Glu Ile Pro Ser Asp Leu Pro Arg Asn Ala Ile Glu Leu
 60                  65                  70                  75

AGG TTT GTC CTC ACC AAG CTT CGA GTC ATC CAA AAA GGT GCA TTT TCA      410
Arg Phe Val Leu Thr Lys Leu Arg Val Ile Gln Lys Gly Ala Phe Ser
                 80                  85                  90

GGA TTT GGG GAC CTG GAG AAA ATA GAG ATC TCT CAG AAT GAT GTC TTG      458
Gly Phe Gly Asp Leu Glu Lys Ile Glu Ile Ser Gln Asn Asp Val Leu
             95                 100                 105

GAG GTG ATA GAG GCA GAT GTG TTC TCC AAC CTT CCC AAA TTA CAT GAA      506
Glu Val Ile Glu Ala Asp Val Phe Ser Asn Leu Pro Lys Leu His Glu
        110                 115                 120

ATT AGA ATT GAA AAG GCC AAC AAC CTG CTC TAC ATC AAC CCT GAG GCC      554
Ile Arg Ile Glu Lys Ala Asn Asn Leu Leu Tyr Ile Asn Pro Glu Ala
    125                 130                 135

TTC CAG AAC CTT CCC AAC CTT CAA TAT CTG TTA ATA TCC AAC ACA GGT      602
Phe Gln Asn Leu Pro Asn Leu Gln Tyr Leu Leu Ile Ser Asn Thr Gly
140                 145                 150                 155

ATT AAG CAC CTT CCA GAT GTT CAC AAG ATT CAT TCT CTC CAA AAA GTT      650
Ile Lys His Leu Pro Asp Val His Lys Ile His Ser Leu Gln Lys Val
                160                 165                 170

TTA CTT GAC ATT CAA GAT AAC ATA AAC ATC CAC ACA ATT GAA AGA AAT      698
```

-continued

```
Leu Leu Asp Ile Gln Asp Asn Ile Asn Ile His Thr Ile Glu Arg Asn
            175                 180                 185

TCT TTC GTG GGG CTG AGC TTT GAA AGT GTG ATT CTA TGG CTG AAT AAG      746
Ser Phe Val Gly Leu Ser Phe Glu Ser Val Ile Leu Trp Leu Asn Lys
        190                 195                 200

AAT GGG ATT CAA GAA ATA CAC AAC TGT GCA TTC AAT GGA ACC CAA CTA      794
Asn Gly Ile Gln Glu Ile His Asn Cys Ala Phe Asn Gly Thr Gln Leu
    205                 210                 215

GAT GAG CTG AAT CTA AGC GAT AAT AAT AAT TTA GAA GAA TTG CCT AAT      842
Asp Glu Leu Asn Leu Ser Asp Asn Asn Asn Leu Glu Glu Leu Pro Asn
220                 225                 230                 235

GAT GTT TTC CAC GGA GCC TCT GGA CCA GTC ATT CTA GAT ATT TCA AGA      890
Asp Val Phe His Gly Ala Ser Gly Pro Val Ile Leu Asp Ile Ser Arg
                240                 245                 250

ACA AGG ATC CAT TCC CTG CCT AGC TAT GGC TTA GAA AAT CTT AAG AAG      938
Thr Arg Ile His Ser Leu Pro Ser Tyr Gly Leu Glu Asn Leu Lys Lys
            255                 260                 265

CTG AGG GCC AGG TCG ACT TAC AAC TTA AAA AAG CTG CCT ACT CTG GAA      986
Leu Arg Ala Arg Ser Thr Tyr Asn Leu Lys Lys Leu Pro Thr Leu Glu
        270                 275                 280

AAG CTT GTC GCC CTC ATG GAA GCC AGC CTC ACC TAT CCC AGC CAT TGC     1034
Lys Leu Val Ala Leu Met Glu Ala Ser Leu Thr Tyr Pro Ser His Cys
    285                 290                 295

TGT GCC TTT GCA AAC TGG AGA CGG CAA ATC TCT GAG CTT CAT CCA ATT     1082
Cys Ala Phe Ala Asn Trp Arg Arg Gln Ile Ser Glu Leu His Pro Ile
300                 305                 310                 315

TGC AAC AAA TCT ATT TTA AGG CAA GAA GTT GAT TAT ATG ACT CAG ACT     1130
Cys Asn Lys Ser Ile Leu Arg Gln Glu Val Asp Tyr Met Thr Gln Thr
                320                 325                 330

AGG GGT CAG AGA TCC TCT CTG GCA GAA GAC AAT GAG TCC AGC TAC AGC     1178
Arg Gly Gln Arg Ser Ser Leu Ala Glu Asp Asn Glu Ser Ser Tyr Ser
            335                 340                 345

AGA GGA TTT GAC ATG ACG TAC ACT GAG TTT GAC TAT GAC TTA TGC AAT     1226
Arg Gly Phe Asp Met Thr Tyr Thr Glu Phe Asp Tyr Asp Leu Cys Asn
        350                 355                 360

GAA GTG GTT GAC GTG ACC TGC TCC CCT AAG CCA GAT GCA TTC AAC CCA     1274
Glu Val Val Asp Val Thr Cys Ser Pro Lys Pro Asp Ala Phe Asn Pro
    365                 370                 375

TGT GAA GAT ATC ATG GGG TAC AAC ATC CTC AGA TAGCTGCAG               1316
Cys Glu Asp Ile Met Gly Tyr Asn Ile Leu Arg
380                 385                 390
```

(2) INFORMATION FOR SEQ ID NO:2:

(i) SEQUENCE CHARACTERISTICS:
(A) LENGTH: 390 amino acids
(B) TYPE: amino acid
(D) TOPOLOGY: linear (ii) MOLECULE TYPE: peptide (xi) SEQUENCE DESCRIPTION: SEQ ID NO:2:

```
Met Leu Leu Val Asn Gln Ser His Gln Gly Phe Asn Lys Glu His Thr
  1               5                  10                  15

Ser Lys Met Val Ser Ala Ile Val Leu Tyr Val Leu Leu Ala Ala Ala
             20                  25                  30

Ala His Ser Ala Phe Ala Ala Asp Gln Cys His His Arg Ile Cys His
         35                  40                  45

Cys Ser Asn Arg Val Phe Leu Cys Gln Glu Ser Lys Val Thr Glu Ile
     50                  55                  60
```

-continued

```
Pro Ser Asp Leu Pro Arg Asn Ala Ile Glu Leu Arg Phe Val Leu Thr
 65                  70                  75                  80

Lys Leu Arg Val Ile Gln Lys Gly Ala Phe Ser Gly Phe Gly Asp Leu
                 85                  90                  95

Glu Lys Ile Glu Ile Ser Gln Asn Asp Val Leu Glu Val Ile Glu Ala
            100                 105                 110

Asp Val Phe Ser Asn Leu Pro Lys Leu His Glu Ile Arg Ile Glu Lys
        115                 120                 125

Ala Asn Asn Leu Leu Tyr Ile Asn Pro Glu Ala Phe Gln Asn Leu Pro
    130                 135                 140

Asn Leu Gln Tyr Leu Leu Ile Ser Asn Thr Gly Ile Lys His Leu Pro
145                 150                 155                 160

Asp Val His Lys Ile His Ser Leu Gln Lys Val Leu Leu Asp Ile Gln
                165                 170                 175

Asp Asn Ile Asn Ile His Thr Ile Glu Arg Asn Ser Phe Val Gly Leu
            180                 185                 190

Ser Phe Glu Ser Val Ile Leu Trp Leu Asn Lys Asn Gly Ile Gln Glu
        195                 200                 205

Ile His Asn Cys Ala Phe Asn Gly Thr Gln Leu Asp Glu Leu Asn Leu
    210                 215                 220

Ser Asp Asn Asn Asn Leu Glu Glu Leu Pro Asn Asp Val Phe His Gly
225                 230                 235                 240

Ala Ser Gly Pro Val Ile Leu Asp Ile Ser Arg Thr Arg Ile His Ser
                245                 250                 255

Leu Pro Ser Tyr Gly Leu Glu Asn Leu Lys Lys Leu Arg Ala Arg Ser
            260                 265                 270

Thr Tyr Asn Leu Lys Lys Leu Pro Thr Leu Glu Lys Leu Val Ala Leu
        275                 280                 285

Met Glu Ala Ser Leu Thr Tyr Pro Ser His Cys Cys Ala Phe Ala Asn
    290                 295                 300

Trp Arg Arg Gln Ile Ser Glu Leu His Pro Ile Cys Asn Lys Ser Ile
305                 310                 315                 320

Leu Arg Gln Glu Val Asp Tyr Met Thr Gln Thr Arg Gly Gln Arg Ser
                325                 330                 335

Ser Leu Ala Glu Asp Asn Glu Ser Ser Tyr Ser Arg Gly Phe Asp Met
            340                 345                 350

Thr Tyr Thr Glu Phe Asp Tyr Asp Leu Cys Asn Glu Val Val Asp Val
        355                 360                 365

Thr Cys Ser Pro Lys Pro Asp Ala Phe Asn Pro Cys Glu Asp Ile Met
    370                 375                 380

Gly Tyr Asn Ile Leu Arg
385                 390
```

(2) INFORMATION FOR SEQ ID NO:3:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: oligonucleotide (xi) SEQUENCE DESCRIPTION: SEQ ID NO:3:

```
TTTTTGATCA GTGTCATCAT CGGATCTGTC                                   30
```

-continued (2) INFORMATION FOR SEQ ID NO:4:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: oligonucleotide (xi) SEQUENCE DESCRIPTION: SEQ ID NO:4:

TTTTCTGCAG CTATCTGAGG ATGTTGTACC CC 32

(2) INFORMATION FOR SEQ ID NO:5:

(i) SEQUENCE CHARACTERISTICS:
(A) LENGTH: 38 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:5:

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala
        35
```

(2) INFORMATION FOR SEQ ID NO:6:

(i) SEQUENCE CHARACTERISTICS:
(A) LENGTH: 18 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:6:

```
Met Thr Ile Leu Cys Trp Leu Ala Leu Leu Ser Thr Leu Thr Ala Val
1               5                   10                  15

Asn Ala
```

(2) INFORMATION FOR SEQ ID NO:7:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:7:

```
Met Val Ser Ala Ile Val Leu Tyr Val Leu Leu Ala Ala Ala Ala His
1               5                   10                  15

Ser Ala Phe Ala Ala Glu His Cys
            20
```

(2) INFORMATION FOR SEQ ID NO:8:

(i) SEQUENCE CHARACTERISTICS:
(A) LENGTH: 19 amino acids
(B) TYPE: amino acid

-continued (C) STRANDEDNESS: single
(D) TOPOLOGY: linear (ii) MOLECULE TYPE: peptide (xi) SEQUENCE DESCRIPTION: SEQ ID NO:8:

```
Met Tyr Lys Leu Thr Val Phe Leu Met Phe Ile Ala Phe Val Ile Ile
1               5                   10                  15

Ala Glu Ala
```

(2) INFORMATION FOR SEQ ID NO:9:

(i) SEQUENCE CHARACTERISTICS:
(A) LENGTH: 22 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

```
Met Val Gln Arg Cys Leu Val Val Ala Leu Leu Val Val Val Val Ala
1               5                   10                  15

Ala Ala Leu Cys Ser Ala
            20
```

(2) INFORMATION FOR SEQ ID NO:10:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:10:

```
Met Phe Lys Phe Val Met Ile Cys Ala Val Leu Gly Leu Ala Val Ala
1               5                   10                  15
```

(2) INFORMATION FOR SEQ ID NO:11:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:11:

```
Met Phe Lys Phe Val Met Ile Leu Ala Val Val Gly Val Ala Thr Ala
1               5                   10                  15
```

(2) INFORMATION FOR SEQ ID NO:12:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

```
Met Phe Lys Ile Leu Leu Val Cys Ser Leu Ala Ala Leu Val Ala Ala
1               5                   10                  15
```

```
(2) INFORMATION FOR SEQ ID NO:13:

     (i) SEQUENCE CHARACTERISTICS:
          (A) LENGTH: 11 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:13:

Met Phe Lys Ile Leu Leu Val Cys Ala Leu Val
1               5                   10


(2) INFORMATION FOR SEQ ID NO:14:

     (i) SEQUENCE CHARACTERISTICS:
          (A) LENGTH: 17 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:14:

Met Phe Leu Ala Lys Ser Ile Val Cys Leu Ala Leu Leu Ala Val Ala
1               5                   10                  15

Asn


(2) INFORMATION FOR SEQ ID NO:15:

     (i) SEQUENCE CHARACTERISTICS:
          (A) LENGTH: 20 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:15:

Met Ser Thr Phe Ala Phe Leu Leu Leu Cys Ile Gln Ala Cys Leu Ile
1               5                   10                  15

Gln Asn Val Tyr
            20


(2) INFORMATION FOR SEQ ID NO:16:

     (i) SEQUENCE CHARACTERISTICS:
          (A) LENGTH: 21 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:16:

Met Asn Phe Ser Arg Ile Phe Phe Phe Val Phe Ala Leu Val Leu Ala
1               5                   10                  15

Leu Ser Thr Ala Ser
            20


(2) INFORMATION FOR SEQ ID NO:17:

     (i) SEQUENCE CHARACTERISTICS:
          (A) LENGTH: 21 amino acids
          (B) TYPE: amino acid
          (C) STRANDEDNESS: single
```

-continued

```
        (D) TOPOLOGY: linear

    (ii) MOLECULE TYPE: peptide

    (xi) SEQUENCE DESCRIPTION: SEQ ID NO:17:

Met Asn Phe Ser Arg Ile Phe Phe Phe Val Phe Ala Leu Val Leu Ala
1               5                   10                  15

Leu Ser Thr Val Ser
            20


(2) INFORMATION FOR SEQ ID NO:18:

     (i) SEQUENCE CHARACTERISTICS:
          (A) LENGTH: 26 amino acids
          (B) TYPE: amino acid
          (C) STRANDEDNESS: single
          (D) TOPOLOGY: linear

    (ii) MOLECULE TYPE: peptide

    (xi) SEQUENCE DESCRIPTION: SEQ ID NO:18:

Met Ala Met Ile Pro Ser Ile Ser Lys Leu Leu Phe Val Ala Ile Cys
1               5                   10                  15

Leu Phe Val Tyr Met Gly Leu Ser Phe Gly
            20                  25
```

METHOD OF EXPRESSING AND SECRETING SOLUBLE EXTRACELLULAR DOMAINS OF HUMAN GONADOTROPIN HORMONE RECEPTORS

BACKGROUND OF THE INVENTION

1. Field of the Invention

The invention relates to a method of generating soluble extracellular domains of human gonadotropin hormone receptors in functional form by expression and secretion in the baculovirus/insect cell system. The invention is also related to a recombinant baculovirus transfer vector carrying DNA encoding the soluble receptor extracellular domains, insect cells expressing and secreting the soluble receptor extracellular domains, and a method of purifying these same soluble receptor extracellular domains.

2. Description of the Background Art

Follicle stimulating hormone (FSH), luteinizing hormone (LH), chorionic gonadotropin (CG), and thyroid stimulating hormone (TSH) are large heterodimeric glycoproteins having a molecular weight of approximately 28–38 kDa and composed of a common α subunit non-covalently bound to a specific β subunit that confers receptor binding specificity. While FSH, LH, and CG are classified as gonadotropins, TSH is not. However, TSH is considered a gonadotropin-like hormone by virtue of sharing many common characteristics with the gonadotropins FSH, LH, and CG. This family of gonadotropin/gonadotropin-like glycoprotein hormones all interact selectively with specific receptors comprising a subclass in the superfamily of G protein-coupled receptors which display seven transmembrane spanning segments as part of their transmembrane domain.

Like other known families of G protein-coupled receptors, the glycoprotein hormone receptors have an extracellular domain and a cytoplasmic tail in addition to the distinctive transmembrane domain. However, the glycoprotein hormone receptor family is distinguished from other G protein-coupled receptors, such as rhodopsin, β2-adrenergic receptors, etc., by the large size (>300 amino acid residues) of its extracellular domain or "ectodomain," which also contains multiple cysteine residues and N-linked glycosylation sites. Upon activation by their respective hormone ligands, the glycoprotein hormone receptors stimulate an increase in adenylyl cyclase activity and elevated intracellular adenosine 3', 5'-cyclic phosphate (cAMP) levels (Verrier et al., *Eur. J. Biochem.,* 74:243–252, 1977; Hunzicker-Dunn et al., in *Luteinizing Hormone Action and Receptors*, p. 57, 1985, CRC Press, Boca Raton, Fla.; Field, in *The Thyroid*, p. 288, 1986, JB Lippencott Co., Philadelphia, Pa).

The binding specificity of the glycoprotein hormone receptor and its hormone ligand appears to reside principally in the extracellular portion of the receptor. In studies with the LH receptor, variants of the LH receptor molecule lacking the transmembrane domain and the C-terminal regions have been found to bind LH with high specificity and affinity (Tsai-Morris et al., *J. Biol. Chem.* 265:19385–19388, 1990; Xie et al., *J. Biol. Chem.* 265:21411–21414, 1991). Binding specificity has also been found to be conferred by the extracellular domain in chimeric glycoprotein hormone receptors created by interchanging N-terminal portions that include the extracellular domain (Braun et al., *EMBO J.* 10:1885–1890, 1991; Nagayama et al., *Biochem. Biophys. Res. Commun.* 173:1150–1156, 1990 and *Proc Natl. Acad. Sci. USA* 88:902–905, 1991). Davis et al., *Mol. Endocrinol.* 9:159–170, (1995) recently reported that the expression of the extracellular domain of rat FSHR by itself is sufficient for high affinity interactions with human FSH.

Although the extracellular high affinity hormone-binding domain of the rat LH receptor has been shown to be expressed independently of the domain that anchors the receptor in the cell membrane, the expressed extracellular domain was found to be retained intracellularly in the human kidney and COS host cells (Xie et al., *J. Biol. Chem.* 265:21411–21414, 1990; Moyle et al., *J. Biol. Chem* 266:10807–10812, 1991; Ji et al., *Endocrinology* 128:2648–2650, 1991; Pajot-Augy et al., *J. Mol. Endocrinol.* 14:51–66, 1995) with the exception of one study (Tsai-Morris et al., *J. Biol. Chem.* 265:19385–19388, 1990). Tsai-Morris et al., supra, reportedly found a naturally occurring soluble variant of the LH receptor, which is believed to be a product of alternative splicing, being secreted extracellularly by COS-7 cells. However, when Moyle et al., supra, expressed this same variant in COS-7 cells, they were unable to reproduce the secretion of soluble modified LH receptor into the culture medium. Instead, they observed that the LHR analogs or variants lacking the transmembrane domain were predominantly retained inside the cell. Kolena et al., *Endocrinol. Exp.* 20:339–348 (1993) and Wimalasena et al., *Endocrinol.* 113:618–624 (1983) reported the existence of naturally occurring soluble LH/CG binding proteins which might be receptor fragments. Bernard et al., *Mol. Cell. Endocrinol.* 71:R1914 R23 (1990) reported that alternatively spliced mRNA encoding a truncated LH receptor was expressed in rat ovary which may be an explanation for the previously reported soluble LH receptors. In a separate study with a truncated form (346 N-terminal amino acids) of rat FSHR representing the extracellular domain, it was reported that this truncated receptor was not secreted from human embryonic kidney cells, but rather trapped intracellularly despite the presence of a signal peptide and the absence of any membrane anchoring regions (Davis et al., supra).

The extracellular domain of the LH receptor was efficiently expressed in *E. coli* as a truncated receptor which formed inclusion bodies that required refolding with a mild denaturant, guanidine-HCl, to generate a multimeric hormone binding-component soluble form of the receptor (Chen et al., *Mol. Cell. Endocrinol.* 91:35–41, 1993). As heterologous proteins are expressed in *E. coli* host cells in nonglycosylated form, the work of Chen and coworkers suggests that the N-terminal 1–294 amino acid sequence of the LH receptor appears to have all the necessary information required for proper folding and that carbohydrate moieties on the soluble receptor are not required for proper folding or hormone binding activity of the soluble receptor extracellular domain. In contrast, Davis et al., supra, concluded from the results of their studies on N-linked glycosylation of rat FSHR, that while N-linked rat FSHR carbohydrates do not directly provide a binding site for the hormone, they instead appear to be required for proper folding of nascent receptors into a hormone-binding competent configuration.

A number of research groups have tried to take advantage of the baculovirus/insect cell system to overexpress gonadotropin-like hormone receptors either in full length or as truncated soluble receptor forms. The baculovirus/insect cell expression system offers the advantages of having strong or moderately strong promoters available for the high level expression of a heterologous protein as well as being noninfectious to vertebrates. This helper virus-independent expression system has been used to express heterologous proteins from a variety of different eukaryotes, prokaryotes, and viruses at levels up to 25% of total insect cell protein.

Full length rat FSHR and human FSHR were reported to have been expressed in the baculovirus/insect cell system as functional receptors (Liu et al, *Endocrinol.* 135:682–691, 1994; Christophe et al., *Biochem. Biophys. Res. Commun.* 196:402–408, 1993). However, no provisions for secretion of the soluble extracellular form of the receptor into the culture media was described in either case. Similarly, EP 0614975 A1 relates to the purification and cloning of receptors for LH, CG, FSH, and TSH but only specifically discloses examples with rat luteal LH/CG receptor and rat testicular FSH receptor. Again, no provisions for the secretion of a soluble extracellular form of the receptor was disclosed.

Tilly et al. (*Society For The Study of Reproduction*, vol. 46, supplement 1, abstract #330, 1992) reported the expression of a hormone-binding extracellular domain of hFSHR which was retained intracellularly in the soluble cell fraction of human fetal kidney cells. No secretion of soluble hFSHR receptor was ever disclosed.

Seetharamaiah et al. (*Autoimmunity* 14:315–320, 1993) disclosed that the hTSHR-EC domain of amino acid residues 1–395, was expressed in a baculovirus/insect cell system and obtained from whole cell lysates with no secreted receptor being detected in the culture media as no sequence encoding a signal peptide was present in the gene construct. In a later study, Seetharamaiah et al. (*Endocrinol.* 134:549–554, 1994) also reported the expression of hTSHR-EC in Sf9 insect cells where the receptor was obtained as protein aggregates from whole cell extracts and solubilization with guanidine-HCl was required for proper refolding into a soluble hormone-binding competent configuration.

In contrast, Huang et al. (*J. Mol. Endocrinol.* 10:127–142, 1993) reported the expression in a baculovirus/insect cell system of hTSHR-EC which failed to bind TSH hormone. The gene sequence encoding hTSHR-EC included the endogenous human signal sequence. Very minute amounts of truncated receptor, detectable in SDS-PAGE only when labeled with $^{35}S$, were found to be secreted, with almost all of the hTSHR-EC produced being retained intracellularly.

To summarize previous reports describing expression of extracellular domain of gonadotropin or gonadotropin-like receptors, the expressed truncated receptor was found to be trapped intracellularly, frequently in a non-functional form that requires further purification and refolding with a mild denaturant in order to obtain soluble hormone-binding competent receptor. Even gene constructs that included a signal sequence to facilitate secretion in host cells were unsuccessful in achieving any significant secretion of soluble receptors, functionally hormone-binding or otherwise. Previously, it has not been possible to reproducibly demonstrate secretion of any soluble gonadotropin or gonadotropin-like receptor. A possible explanation for this failure to secrete soluble hormone-binding receptors may be due to soluble receptors being identified as misfolded proteins by the cell and retained for degradation (Klauser et al., *Cell* 62:611–614 (1990)).

Citation of any document herein is not intended as an admission that such document is pertinent prior art, or considered material to the patentability of any claim of the present application. Any statement as to content or a date of any document is based on the information available to the applicant at the time of filing and does not constitute an admission as to the correctness of such a statement.

SUMMARY OF THE INVENTION

The present invention provides a method of expressing and secreting the soluble extracellular domain, fragments or variants thereof, of human gonadotropin hormone receptors in a functional hormone-binding form. The baculovirus/insect cell system is advantageously used in generating these soluble receptors.

The method of the present invention overcomes the difficulty of expressing and secreting soluble receptors in a correctly folded and hormone-binding competent form, as previously encountered in the art, by replacing the native human signal sequence with a baculovirus signal sequence capable of promoting correct folding and secretion in insect host cells.

It is therefore an object of the invention to overcome the deficiencies in the prior art by providing a method of expressing and secreting the soluble extracellular domain of gonadotropin hormone receptors.

Another object of the invention is to provide a recombinant baculovirus transfer vector carrying the DNA encoding the extracellular domain of gonadotropin hormone receptors.

A further object of the invention is to provide insect cells infected with recombinant baculovirus and which express and secrete soluble receptor extracellular domains.

Yet another object of the invention is to provide a method of purifying the soluble receptor extracellular domains secreted by insect cells into the culture media.

BRIEF DESCRIPTION OF THE DRAWINGS

FIGS. 3A–3B shows the nucleotide sequence (SEQ ID NO: 1) of the gene segment encoding the hFSHR-EC fused to a signal sequence and operably linked to a polyhedrin promoter sequence in the pAcGP67-hFSHR-EC transfer vector of FIG. 1. The amino acid sequence (SEQ ID NO: 2) of the translational fusion of hFSHR-EC to the gp67 signal peptide is also shown with the numbering beginning with Met residue of the gp67 signal peptide. The arrow indicates the presumed cleavage site of the gp67 signal peptide.

FIG. 7 shows a UV chromatogram at 280 nm of the 0.5 M NaCl washing (fraction E) and elution of hFSHR-EC with 0.1 M acetic acid (fractions J-M) from the FSH-ligand affinity column.

DETAILED DESCRIPTION OF THE INVENTION

Figure 1:
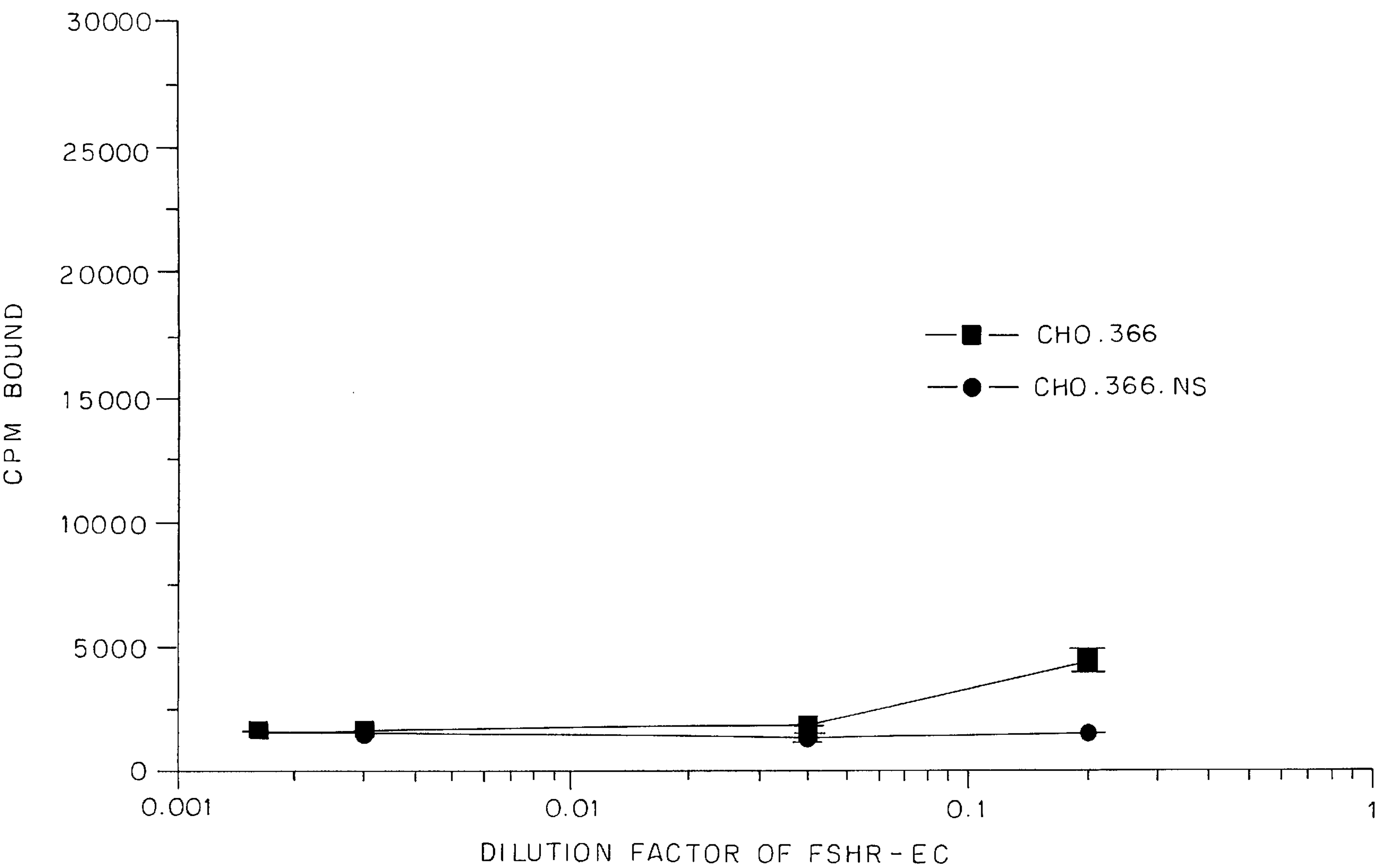
FIG. 1 shows the specific binding of CHO-derived soluble hFSHR-EC to $^{125}$I-hFSH where the amount of $^{125}$I-hFSH bound, expressed as cpm bound, was measured with increasing receptor concentrations (or increasing dilution factors) from left to right along the x-axis.

The present invention provides a method for expressing and secreting the extracellular domain, or fragment thereof, of a gonadotropin hormone receptor in a soluble and functional (hormone-binding competent) form. The method first involves the construction of a recombinant molecule carrying a gene segment, which encodes the extracellular domain of the gonadotropin hormone receptor joined in translational reading frame with a gene segment encoding a baculovirus signal peptide, operably linked to a baculovirus promoter. After construction of this recombinant molecule, co-transfection with baculovirus DNA leads to recombinant baculovirus particles which are then used to infect insect host cells to produce soluble gonadotropin receptors that are secreted into the culture medium.

The term "gonadotropin", as used herein, for hormone receptors is intended to include glycoprotein hormone receptors of FSH, LH, and CG that are classified as gonadotropin receptors and together form a subclass of the G protein-coupled receptor superfamily.

Preferably, the gonadotropin receptors and the extracellular domain expressed and secreted in the present invention are human receptors which are capable of recognizing and selectively binding their corresponding human glycoprotein hormone. While soluble hormone receptors are useful in diagnostic assays, soluble human glycoprotein receptors, which would not be expected to produce any significant immunological response in humans, can also be used in vivo to modulate hormone action in humans.

The nucleotide sequences of human testis FSHR (Kelton et al., *Mol. Cell. Endocrin.* 89:141–151, 1992), human ovary FSHR (Minegishi et al., *Biochem. Biophys. Res. Commun.* 175:1125–1130, 1991), and human LH/CG receptor (Minegishi et al., *Biochem. Biophys. Res. Commun.* 172:1049–1054, 1990) are published and available for use in constructing the recombinant molecule for expression and secretion of extracellular domains of these human gonadotropin hormone receptors. It has been shown that the high affinity hormone-binding site resides in the extracellular domain of these gonadotropin receptors.

In expressing the extracellular domain of gonadotropin receptors in insect host cell systems such as *Spodoptera frugiperda* and *Trichoplusia ni*, a baculovirus promoter is used according to the present invention. The baculovirus late promoters (e.g., 39K protein promoter, basic protein promoter) or very late promoters (e.g., p10 promoter, polyhedrin promoter) are preferred for promoting the transcription of an "operably linked" gene sequence encoding a receptor extracellular domain. The polyhedrin and p10 promoters, which are expressed during the very late phase of viral infection, are considered very strong promoters capable of expressing large amounts of recombinant protein. While the basic protein promoter and 39K protein promoter are both moderately strong promoters expressed during the late phase of baculovirus expression, they may indirectly provide for better post-translational modification of expressed protein. As more modifying enzymes are present during the late phase of the baculovirus infection cycle than during the very late phase, the expression from promoters expressed in the late phase of infection may facilitate any post-translational modifications needed.

A nucleic acid molecule, such as DNA, is said to be "capable of expressing" a polypeptide, such as the extracellular domain of gonadotropin hormone receptors, if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The regulatory regions needed for gene expression in general include a promoter region as well as the DNA sequences which, when transcribed into RNA, will signal the initiation of protein synthesis. Such regions will normally include those 5'-non-coding sequences involved with initiation of transcription and translation.

Two DNA sequences (such as a promoter region sequence and a coding sequence) are said to be operably linked if the nature of the linkage between the two DNA sequences does not (1) result in the introduction of a frame-shift mutation, (2) interfere with the ability of the promoter region sequence to direct the transcription of the coding sequence, or (3) interfere with the ability of the coding sequence to be transcribed by the promoter region sequence. A promoter region would be operably linked to a DNA sequence if the promoter were capable of effecting transcription of that DNA sequence. Thus, to express the protein, transcriptional and translational signals recognized by the host cell are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on the DNA or RNA and is transcribed by the RNA polymerase.

Table 1 lists examples of baculovirus signal peptide (leader) sequences or other insect cell signal peptide sequences that have been reported to facilitate the secretion of heterologous proteins in the baculovirus/insect cell expression systems.

TABLE 1

Signal sequences used for protein expression and secretion in baculovirus/insect cells

| Protein(s) expressed | Species of origin, associated protein, and sequence of signal peptide used for expression and secretion. | | Reference |
|---|---|---|---|
| HIV-1 gp120 | baculovirus ecdysteroid UDPglucosyltransferase (egt) | SEQ ID NO:6 | 1 |
| | baculovirus surface glycoprotein p67 | SEQ ID NO:7 | |
| CD4 | Adipokinetic hormone (AKH) from Lepidoptera *Manduca sexta* | SEQ ID NO:8 | 2, 3, 4 |
| CD4 | Orthoptera *Schistocerca gregaria* AKH | SEQ ID NO:9 | 3, 4 |
| | Diptera Drosophila melanogaster (DDM) cuticle protein-1 (CP1) | SEQ ID NO:10 | |
| | DDM CP2 | SEQ ID NO:11 | |
| | DDM CP3 | SEQ ID NO:12 | |
| | DDM CP4 | SEQ ID NO:13 | |
| Plasminogen activator, Urokinase | *D. meanogaster* α-amylase | SEQ ID NO:14 | 5 |
| | *A. polyhemus* chorion A | SEQ ID NO:15 | |
| | *H. cecropia* cecropin B | SEQ ID NO:16 | |
| | | SEQ ID NO:17 | |
| Herpes simplex virus Type 1 glycoprotein gD, Propapain | *Apis melifica* honeybee melittin | SEQ ID NO:18 | 6, 7 |

1 Murphy et al., Protein Expression and Purification 4:349–357 (1993).
2 Summers et al., U.S. Pat. No. 5,023,328.
3 Summers, U.S. Pat. No. 5,155,037.
4 Summers, U.S. Pat. No. 5,278,050.
5 Clark et al., WO 90/05783.
6 Tessier et al., Gene 98:177–183 (1991).
7 Sisk et al., J. Virol. 68:766–775 (1994).

According to the method of the present invention, the soluble extracellular domain of gonadotropin hormone receptors are expressed and secreted from the baculovirus/insect host cell system. To effect secretion of the receptor extracellular domain in insect host cells, the extracellular domain is expressed together with a baculovirus signal peptide as a fusion protein. While it is possible that other baculovirus signal or leader sequences may facilitate secretion of significant amounts of receptor extracellular domain, the baculovirus gp67 envelope surface glycoprotein signal peptide from *Autographa californica* is the preferred signal peptide sequence for fusion with a receptor extracellular domain. By ligating DNA encoding for the gp67 signal peptide (SEQ ID NO: 5), to the gene segment encoding for the receptor extracellular domain, a fusion protein can be expressed which allows for a soluble extracellular domain of a gonadotropin hormone receptor to be correctly processed through the insect host cell secretory pathway and secreted into the culture medium in a functional and high affinity hormone-binding form.

The manner in which the signal sequence is ligated to the gene segment encoding for a receptor extracellular domain as well as the manner in which a baculovirus promoter sequence is placed 5' to the signal sequence can be achieved in a variety of ways by those of skill in the art. The ligations may be accomplished with blunt-ended termini or staggered-ended termini having partially or completely complementary staggered ends, or ends created artificially by oligonucleotide primers, such as used for site-specific mutagenesis and PCR amplification, and may be performed in any order depending on the chosen cloning strategy.

Factors to be considered in constructing an operably linked promoter-signal sequence-gene fragment of interest as a contiguous segment for expression in insect cells include (1) keeping the 5' untranslated sequence between the promoter sequence and the ATG translational initiation codon to a minimum, with up to approximately 100 nucleotides being generally acceptable;

(2) being careful not to introduce any additional ATG codon, whether out of frame or in frame with the coding sequence, that is 5' to the coding sequence for the gene of interest, as translation normally initiates from the first ATG codon encountered 3' of the baculovirus promoter;

(3) whether or not to create additional amino acid residues or delete amino acid residues at the N-terminus of the receptor extracellular domain by the strategy used to join the signal sequence to the gene fragment of interest.

Variants of the extracellular domain of gonadotropin receptors are included in the soluble receptors to be expressed and secreted by the method of the present invention, some of which can be obtained by modifying the sequence at the junction between the signal sequence and the gene fragment of interest.

In order to introduce the operably linked promoter-signal sequence-gene fragment of interest construct into insect cells and generate soluble gonadotropin hormone receptors that are secreted into the culture medium, the entire construct must be part of a baculovirus transfer vector. Insect cells can be transfected or co-transfected to produce recombinant baculoviruses. In the case of transfection, a baculovirus transfer vector may be recombined with another vector, such as a baculovirus shuttle vector, or "bacmid", etc., and the resultant recombinant baculovirus shuttle vector containing the promoter-signal sequence-gene fragment of interest can then be isolated for transfection into insect cells. The BAC-TO-BAC™ expression system available from GIBCO BRL, Gaithersburg, Md., is an example of using transfection alone to introduce a recombinant baculovirus shuttle vector containing the promoter-signal sequence-gene fragment of interest as an expression cassette. In co-transfection, the baculovirus transfer vector, containing sequence homology to baculovirus DNA, allows for homologous recombination with the co-transfected baculovirus DNA and recombinant baculoviruses can then be either screened or selected.

Additionally, a baculovirus transfer vector may advantageously carry a viral or bacterial origin of replication to allow for amplification of the vector construct in bacteria prior to co-transfection of insect host cells.

It will be understood that co-transfection of the baculovirus transfer vector (carrying the soluble receptor construct)

with baculovirus DNA provides a means of generating recombinant baculoviruses by allowing for homologous recombination between the baculovirus DNA and the baculovirus transfer vector. Therefore, the baculovirus transfer vector used in co-transfection with baculovirus DNA would necessarily carry a region homologous with baculovirus DNA, such as the polyhedrin locus. To improve recombination efficiency, a modified baculovirus DNA carrying a polyhedrin promoter-driven lacZ gene coding for β-galactosidase can be linearized at a single site with a restriction enzyme and recombinants can be screened by their color on X-gal plates where non-recombinants are stained blue (lac Z-positive) and recombinants remain unstained (lac Z-negative) (see AcRP23.lacZ and AcUW1.lacZ baculovirus DNA, Catalogue #21101D and #21102D, respectively, Pharmingen, San Diego, Calif.).

However, it is preferred that the baculovirus transfer vector carry an essential baculovirus gene which can complement a lethal deletion in a modified baculovirus DNA. In this way, only recombinant baculoviruses, where the recombination event has rescued the region complementing the lethal deletion, are selected. A preferred baculovirus transfer vector and modified baculovirus DNA combination is the pAcGP67-A, -B, or -C set of transfer vectors with BACULOGOLD baculovirus DNA, both available from Pharmingen (San Diego, Calif.). BACULOGOLD carries a lethal deletion of an essential gene coded for by the open reading frame 1629 (ORF 1629) which can be rescued by baculovirus transfer vectors carrying ORF-1629 normally located in a region spanning 1.7 Kb downstream from the stop codon of the polyhedrin gene.

Standard reference works setting forth the general principles of recombinant DNA technology include Ausubel et al., eds., *Current Protocols In Molecular Biology*, Green Publishing Assoc. and Wiley Interscience, N.Y. (1987–1994), Watson et al., *Molecular Biology of the Gene*, Volumes I and II, The Benjamin/Cummings Publishing Company, Inc., publisher, Menlo Park, Calif. (1987); Darnell et al., *Molecular Cell Biology*, Scientific American Books, Inc., publisher, New York, N.Y. (1986); Lewin, *Genes II*, John Wiley & Sons, publishers, New York, N.Y. (1985); Old et al., *Principles of Gene Manipulation: An Introduction to Genetic Engineering,* 2d edition, University of California Press, publisher, Berkeley, Calif. (1981); Sambrook et al., *Molecular Cloning: A Laboratory Manual*, Cold Spring Harbor Laboratory, Cold Spring Harbor, N.Y. (1989); and Berger et al., *Guide to Molecular Cloning Techniques*, Methods of Enzymology vol. 152, Academic Press, Inc., publisher, San Diego, Calif., (1987). These references are hereby entirely incorporated by reference.

A number of well-established insect cell lines that are susceptible to baculovirus infection, such as cell lines of *Spodoptera frugiperda* and *Trichoplusia ni*, are readily available. For instance, the *Trichoplusia ni* HIGH-FIVE (BTI-TN-5B1-4) cell line derived from *Trichoplusia ni* egg cell homogenates, can be obtained from Invitrogen (San Diego, Calif.) and *Spodoptera frugiperda* cell lines Sf9 and Sf21, established from ovarial tissues of *S. frugiperda* larvae, can be obtained from Invitrogen or Pharmingen (San Diego, Calif.), ATCC (Catalogue #CRL 1711) among others. In addition, live insect larvae can also be used as the host cell system.

Generally, a first insect cell line is used to generate recombinant baculovirus for viral stock by co-transfection and a second insect cell line is later infected with virus from this recombinant baculovirus stock for the production of soluble gonadotropin-like receptors. The first and second insect cell line used according to the method of the present invention may be the same cell line or may be two different cell lines. In a preferred embodiment, the first insect cell line, that is co-transfected to generate recombinant baculovirus is *Spodoptera frugiperda* Sf9 cell line and the second insect cell line for soluble receptor production is *Trichoplusia ni* HIGH-FIVE cell line.

Protocols for handling of insect cell lines including culturing, co-transfection, assays for viral titer, virus amplification, infection of insect cells, etc., as well as teachings on promoter, vector/DNA, etc., consideration and selection are set forth in Gruenwald et al., *Baculovirus Expression Vector System: Procedures and Methods,* 2nd ed., 1993, Pharmingen, San Diego, Calif.; O'Reilly et al., *Baculovirus Expression Vectors, A Laboratory Manual*, W.H. Freeman and Co., publisher, New York, 1992; Ausubel et al., supra, among other standard reference works in the art. The above references are herein entirely incorporated by reference.

The soluble hormone-binding extracellular domains of gonadotropin hormone receptors expressed and secreted in accordance with the present method can be linked to an affinity column to extract hormone mimetics or antagonists from heterogeneous mixtures such as natural fluids or chemical libraries, and to purify gonadotropin hormones from fluids, extracts, etc. The purified gonadotropin hormones can then be used as therapeutics in the treatment of infertility (FSH), etc.

Like the purified gonadotropin hormone, the soluble hormone-binding extracellular domains can also be used therapeutically, such as to selectively modulate hormone action in vivo. For example, hLH/CGR-EC can be used as a contraceptive agent, with or without coupling to a non-proteinaceous polymer in order to increase the biological half-life of the soluble receptor molecule. Soluble hFSH receptors produced and secreted according to the method of the present invention were found to antagonize FSH binding and stimulation in an in vitro live cell assay. Increasing amounts of added soluble hFSH receptor were observed to block cell stimulation with FSH as monitored by the level of progesterone produced in the live cell assay.

Soluble receptors can also be used in place of monoclonal antibodies to provide solution-based radioligand receptor assays which would detect only receptor-binding competent hormones with virtually no cross-reactivity to free hormone subunits. Similarly, antibody-receptor sandwich assays or enzymatic assays can be performed with the soluble receptor EC domain generated by the method of the present invention.

As the gonadotropin hormones, FSH, LH, and CG bind to their respective glycoprotein hormone receptors with high affinity and specificity, these characteristics make soluble hormone-binding receptors attractive reagents for screening candidate agonists or antagonists.

Other possible diagnostic and therapeutic utilities for which soluble gonadotropin-like hormone receptors would be useful are described in detail in EP 0614975 A1, the contents of which are incorporated herein by reference.

Essentially pure extracellular domains of gonadotropin hormone receptors can also be used in x-ray crystallographic analysis to develop molecular models which define the tertiary structure of the hormone-binding domains. Such information would provide insight into the structure of the actual contact between a hormone and its receptor. Structural information of this sort would be useful in the design of peptides which have gonadotropin-like agonistic or antagonistic activity.

The extracellular domain of gonadotropin receptors to be expressed and secreted according to the method of the present invention can be the entire extracellular domain of these receptors, e.g., amino acid residues 1–349 of the mature hFSHR amino acid sequence beginning with Cys-His-His, variants thereof or fragments/portions of the extracellular domain. Since it appears that the complete extracellular domain is not necessary to bind the corresponding hormone with high affinity, it is contemplated that a fragment or portion of the amino acid terminal extracellular domain may be effectively utilized as a soluble receptor.

Using hFSHR as an example, a fragment which is somewhat shorter than the 349 amino acids of the complete extracellular domain may be readily produced and tested for effective binding to FSH. So long as the hormone-binding region of the extracellular portion is maintained intact, the length of the overall fragment utilized is not critical. For this reason, it is also expected that non-interfering amino acids can be added to either end of the extracellular domain, or hormone-binding fragment thereof, without adversely affecting the hormone-binding capacity of the polypeptide. Accordingly, this invention includes a fragment of the human gonadotropin hormone receptor which comprises a substantial portion of the extracellular domain and which retains substantially the same hormone-binding characteristics as the complete extracellular domain.

Variants or mutant forms of the extracellular domain, or fragment thereof, of the gonadotropin receptors are also intended to be included as the soluble receptors to be expressed and secreted by the method of the present invention. Such variants are those where at least one amino acid residue in the polypeptide has been conservatively replaced by a different amino acid, the location and nature of such substitutions being selected so as not to significantly affect the hormone-binding characteristics of the soluble receptor or fragment thereof which is modified. Thus, the amino acid or nucleic acid sequence of a variant is said to "essentially correspond" to another amino acid or nucleic acid sequence, respectively, if the sequence of amino acids or nucleic acid in both molecules provides polypeptides having biological activity that is essentially similar, qualitatively or quantitatively, to the corresponding polypeptide. Such "essentially corresponding" hormone receptor extracellular domain sequences include conservative amino acid or nucleotide substitutions, or degenerate nucleotide codon substitutions where individual amino acid or nucleotide substitutions are well known in the art.

Accordingly, hormone-binding extracellular domains, fragments thereof, or nucleic acid encoding therefor, include a finite set of essentially corresponding sequences as substitution peptides or polynucleotides which can be routinely obtained by one of ordinary skill in the art, without undue experimentation, based on the teachings and guidance presented herein. For a detailed description of protein chemistry and structure, see Schulz et al., *Principles of Protein Structure*, Springer-Verlag, New York, 1978, and Creighton, *Proteins: Structure and Molecular Properties*, W. H. Freeman & Co., San Francisco, 1983, which are hereby incorporated by reference. For a presentation of nucleotide sequence substitutions, such as codon preferences, see Ausubel et al, eds, *Current Protocols in Molecular Biology*, Greene Publishing Assoc., N.Y. (1987, 1988, 1989, 1990, 1991, 1992, 1993, 1994) at §§ A.1.1–A.1.24, and Sambrook et al, *Molecular Cloning: A Laboratory Manual*, Second Edition, Cold Spring Harbor Press, Cold Spring Harbor, N.Y. (1989), at Appendices C and D.

As mentioned previously, conservative substitutions include variants wherein at least one amino acid residue in the polypeptide has been conservatively replaced by a different amino acid. Such substitutions preferably are made in accordance with the following list as presented in Table 2, which substitutions can be determined by routine experimentation to provide modified structural and functional properties of a synthesized or recombinant polypeptide molecule, while maintaining hormone-binding activity, as determined by radioligand receptor assays, Scatchard analysis, etc. In the context of the present invention, the term "essentially corresponding to" includes such substitutions.

TABLE 2

| Original Residue | Exemplary Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Accordingly, based on the above example of specific substitutions, alternative substitutions can be made by routine experimentation, to provide alternative extracellular domains of gonadotropin receptors, e.g., by making one or more conservative substitutions. Preferably, even such conservative substitutions should be in the non-conserved portions of the extracellular domain. It would be expected that any such substitutions would retain hormone-binding activity, which activity can be checked with routine experimentation, as will be described below.

Alternatively, another group of substitutions are those in which at least one amino acid residue in the protein molecule has been removed and a different residue inserted in its place according to the following Table 3. The types of substitutions which can be made in the protein or peptide molecule can be based on analysis of the frequencies of amino acid changes between a homologous protein of different species or conserved amino acids between the human and other mammalian gonadotropin-like hormone receptors. Based on such an analysis, alternative conservative substitutions are defined herein as exchanges within one of the following five groups:

Table 3

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val, (Cys); and
5. Large aromatic residues: Phe, Tyr, Trp.

The three amino acid residues in parentheses above have special roles in protein architecture. Gly is the only residue lacking any side chain and thus imparts flexibility to the chain. This, however, tends to promote the formation of secondary structure other than α-helical. Pro, because of its unusual geometry, tightly constrains the chain. It generally tends to promote β-turn-like structures. In some cases Cys can be capable of participating in disulfide bond formation which is important in protein folding. Note that Schulz et al. would merge Groups 1 and 2 above. Note also that Tyr, because of its hydrogen bonding potential, has significant kinship with Ser, and Thr, etc. Knowledge of the secondary structure and of the tertiary structure will assist those of skill in the art in determining which such substitutions would not be expected to affect the binding capability of the peptide.

Conservative amino acid substitutions, included in the term "essentially corresponding", according to the present invention, e.g., as presented above, are well known in the art and would be expected to maintain the binding properties of the polypeptide after amino acid substitution. Most deletions and insertions, and substitutions according to the present invention are those which do not produce radical changes in the characteristics of the protein or peptide molecule. "Characteristics" is defined in a non-inclusive manner to define both changes in secondary structure, e.g., α-helix or β-sheet, as well as changes in binding activity.

However, when the exact effect of the substitution, deletion, or insertion is to be confirmed, one skilled in the art will appreciate that the effect of the substitution or substitutions will be evaluated by routine screening assays, such as radioligand receptor assays, ELISA, etc., to confirm biological activity, i.e., hormone-binding.

Most deletions and insertions, and substitutions of the extracellular domain of gonadotropin receptors are those which maintain or improve the hormone-binding characteristics of the protein or peptide molecule. However, when it is difficult to predict the exact effect of the substitution, deletion, or insertion in advance of doing so, one skilled in the art will appreciate that the effect will be evaluated by routine screening assays. For example, a variant made by site-specific mutagenesis of the peptide molecule-encoding nucleic acid and expression of the variant extracellular domain in cell culture can be tested for binding by binding assays disclosed herein, to test gonadotropin hormone-binding capability.

Amino acid sequence variants of the extracellular domain of gonadotropin receptors can be prepared by mutations in the DNA. Such variants include, for example, deletions from, or insertions or substitutions of, residues within the amino acid sequence. Any combination of deletion, insertion, and substitution can also be made to arrive at expressing and producing the final extracellular domain construct, provided that the final construct possesses some hormone-binding activity. Preferably, improved hormone-binding activity is found over that of the non-variant peptide. Obviously, the mutations that will be made in the DNA encoding the variant must not place the sequence out of reading frame and preferably will not create complementary regions that could produce secondary mRNA structure (see, e.g., EP Patent Application Publication No. 75,444, Ausubel et al., supra, 1987–1994; Sambrook et al., supra, 1989).

Amino acid sequence insertions include amino and/or carboxyl-terminal fusions of from one residue to polypeptides of essentially unrestricted length, as well as intrasequence insertions of single or multiple amino acid residues. Intrasequence insertions may range generally from about 1 to 10 residues, more preferably 1 to 5. An example of a terminal insertion includes a fusion of a signal sequence, whether heterologous or homologous to the host cell, to the N-terminus of the receptor extracellular domain to facilitate secretion from recombinant hosts.

At the genetic level, these variants ordinarily are prepared by site-directed mutagenesis of nucleotides in the DNA encoding the extracellular domain of a gonadotropin receptor, thereby producing DNA encoding the variant, and thereafter synthesizing the DNA and expressing the peptide in recombinant cell culture. The variants typically exhibit the same qualitative biological activity as the naturally occurring analogue, Ausubel et al., supra, 1987–1994; Sambrook et al., supra, 1989.

Preparation of an extracellular domain variant in accordance herewith, or an alternative nucleotide sequence encoding the same polypeptide but differing from the natural sequence due to changes permitted by the known degeneracy of the genetic code, can be achieved by site-specific mutagenesis of DNA that encodes an earlier prepared variant or a nonvariant version of the receptor extracellular domain. Site-specific mutagenesis allows the production of variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 complementing nucleotides on each side of the sequence being altered. In general, the technique of site-specific mutagenesis is well known in the art, as exemplified by publications such as Adelman et al., *DNA* 2:183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily available commercially and their use is generally well known to those skilled in the art. Alternatively, plasmid vectors that contain a single-stranded phage origin of replication (Veira et al., *Meth. Enzymol.* 153:3 (1987)) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared synthetically by automated DNA/oligonucleotide synthesis. This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a mutated sequence and the second strand bears the desired mutation. This heteroduplex vector is then used to transform appropriate cells, such as *E. coli* JM101 cells, and clones are selected that include recombinant vectors bearing the mutated sequence arrangement.

After such a clone is selected, the mutated receptor extracellular domain region may be removed and placed in an appropriate vector, generally a transfer or expression vector of the type that may be employed for transfection of an appropriate host.

As previously mentioned above, the nucleotide and amino acid sequences of human gonadotropin receptors as well as a number of gonadotropin receptors from other mammalian species have been published and are readily available to those in the art.

Accordingly, gene or nucleic acid encoding for a gonadotropin hormone receptor having an extracellular domain can also be detected, obtained and/or modified, in vitro, in situ and/or in vivo, by the use of known DNA or RNA amplification techniques, such as PCR and chemical oligonucleotide synthesis. PCR allows for the amplification (increase in number) of specific DNA sequences by repeated DNA polymerase reactions. This reaction can be used as a replacement for cloning; all that is required is a knowledge of the nucleic acid sequence. In order to carry out PCR, primers are designed which are complementary to the sequence of interest. The primers are then generated by automated DNA synthesis. Because primers can be designed to hybridize to any part of the gene, conditions can be created such that mismatches in complementary base pairing can be tolerated. Amplification of these mismatched regions can lead to the synthesis of a mutagenized product resulting in the generation of a peptide with new properties (i.e., site directed mutagenesis). See also, e.g., Ausubel, supra, Ch. 16. Also, by coupling complementary DNA (cDNA) synthesis, using reverse transcriptase, with PCR, RNA can be used as the starting material for the synthesis of the extracellular domain of a gonadotropin receptor without cloning.

Furthermore, PCR primers can be designed to incorporate new restriction sites or other features such as termination codons at the ends of the gene segment to be amplified. This placement of restriction sites at the 5' and 3' ends of the amplified gene sequence allows for gene segments encoding an extracellular domain or fragment thereof to be custom designed for ligation with signal sequences and/or cloning sites in vectors.

PCR and other methods of amplification of RNA and/or DNA are well known in the art and can be used according to the present invention without undue experimentation, based on the teaching and guidance presented herein. Known methods of DNA or RNA amplification include, but are not limited to polymerase chain reaction (PCR) and related amplification processes (see, e.g., U.S. Pat. Nos. 4,683,195, 4,683,202, 4,800,159, 4,965,188, to Mullis et al.; U.S. Pat. Nos. 4,795,699 and 4,921,794 to Tabor et al.; U.S. Pat. No. 5,142,033 to Innis; U.S. Pat. No. 5,122,464 to Wilson et al.; U.S. Pat. No. 5,091,310 to Innis; U.S. Pat. No. 5,066,584 to Gyllensten et al.; U.S. Pat. No. 4,889,818 to Gelfand et al.; U.S. Pat. No. 4,994,370 to Silver et al.; U.S. Pat. No. 4,766,067 to Biswas; U.S. Pat. No. 4,656,134 to Ringold; and Innis et al., eds., *PCR Protocols: A Guide to Method and Applications*) and RNA mediated amplification which uses anti-sense RNA to the target sequence as a template for double stranded DNA synthesis (U.S. Pat. No. 5,130,238 to Malek et al., with the tradename NASBA); and immuno-PCR which combines the use of DNA amplification with antibody labeling (Ruzicka et al., *Science* 260:487 (1993); Sano et al., *Science* 258:120 (1992); Sano et al., *Biotechniques* 9:1378 (1991)), the entire contents of which patents and reference are entirely incorporated herein by reference.

Having now generally described the invention, the same will be more readily understood through reference to the following examples which are provided by way of illustration and is not intended to be limiting of the present invention.

Example 1

Expression and Purification of A Truncated hFSH Receptor Encompassing the Entire hFSHR-EC Domain in CHO-DUKX Cells A human FSHR mutant cDNA, designated FSHR366, was constructed to encompass the whole extracellular domain of full-length hFSHR beginning with Met, of the human signal peptide and truncating at amino acid residue $Arg_{366}$. Additionally, the hFSH truncated receptor also contained a six polyhistidine tail attached to the C-terminal $Arg_{366}$ residue. The DNA fragments encoding hFSHR366 was inserted into an expression vector carrying DHFR which was then used to transfect CHO-DUKX cells. Methotrexate resistent clones were obtained and cultured for analysis of truncated hFSHR expression and for the purification of truncated receptor.

$^{125}$I-FSH specific binding was determined for the cell pellet and cell lysate fractions as well as for the culture media and intact cells. For each sample, the total binding to $^{125}$I-FSH (human) was determined by incubating an aliquot of the test sample with an aliquot of $^{125}$I-FSH at 37° C. The non-specific binding was determined by adding an excess of cold FSH to an identical tube set up for each sample. The specific $^{125}$I-FSH bound radioactive counts in cpm for each sample was calculated by taking the difference between the counts for the total bound $^{125}$I-FSH and the non-specific bound counts.

For the determination of specific FSH binding in cell pellet and cell lysate fractions, 1–5×$10^7$ CHO cells were suspended in 1 ml of 1% Triton in sucrose/Hepes/Mg/Ca buffer and then homogenized on dounce. The suspension was diluted with 9 ml of sucrose/Hepes/Mg/Ca buffer and then spun at 10,000×g for 20 minutes at 4° C. Aliquots of the supernatant were serial diluted and used directly in the binding assay. For the binding assay, 90 ul of the CHO-366 supernatant sample, 10 ul (96,000 cpm, 1.1 nM) of $^{125}$I-hFSH, and 10 ul of $H_2O$ or 1.2 uM rhFSH were combined in Falcon 12×75 mm polypropylene tubes. The solution was incubated at 37° C. for 0.75 hours. The solution was placed on ice and 50 ul of 0.5% (w/v) γ-globulin buffer (in 50 mM Tris, pH 7.35) was added. After 5 minutes, 160 ul of 21% (w/v) PEG-8000 solution (in 50 mM Tris, pH 7.25) was added to each sample. The samples sat on ice for approximately 1 hour. The precipitate was pelleted by spinning at 3750 rpm (ca. 3000 Xg). To bring non-specific binding to less than 15% of total binding, a second precipitation was carried out. The supernatant was aspirated, and the pellet was redissolved in 1 ml of 0.1% (v/v) Triton X-100 in PBS, diluted with 0.5 ml of 0.5% γ-globulin buffer followed by 1.5 ml of PEG-8000 solution. The mixture stood on ice for 30 minutes, then centrifuged at 3750 rpm (ca. 3000 Xg), and the supernatant was aspirated. Pellets were counted on a γ-counter. The specific binding of CHO-derived soluble FSHR-EC to $^{125}$I-hFSHA is shown in FIG. 1.

The specific binding resulting from cell pellet, cell lysate, culture medium, and intact cells demonstrate that hFSHR366 is expressed in CHO cells as a soluble receptor which is found predominantly in the cell lysate or to a much lesser extent in the cell pellet. Insignificant levels of specific $^{125}$I-hFSH binding was observed in the culture medium and intact cell samples. These results indicate that hFSHR366 is not secreted into the culture medium or present on the surface of intact whole cells in significant amounts but rather is trapped intracellularly in CHO cells.

Membrane fractions from cells expressing full-length hFSHR and cell lysates from cells expressing soluble hFSHR366 were processed for Scatchard analysis to measure the FSH binding affinity of soluble and full-length hFSHR. Scatchard analysis was determined by adding increasing amounts of cold FSH to a constant amount of $^{125}$I-FSH and a constant amount of experimental cell sample fraction. The assay contained 30 $\mu$l of cell lysate sample or 10 $\mu$l of membrane, approximately 1.2 ng $^{125}$I-FSH and unlabeled hFSH (in the range of 0 to 4000 ng). The assay was incubated at 4° C., for either 6 hours, or 16–18 hours at which time equilibrium was reached. For Scatchard analysis the affinity constant was the slope of the best-fit line through a plot of the concentration of bound hormone divided by free hormone ([B]/[F]) versus bound hormone ([B]). [B] and [F] were calculated from the specifically bound counts measured in the pellet, the total amounts of r-hFSH and $^{125}$I-FSH added to the reaction, and the known specific activity of the $^{125}$I-FSH following procedures known by those skilled in the art, with the aid of an Excel 4.0 program (Microsoft).

Several anti-peptide human FSHR antibodies were tested for specificity to detect the soluble FSHR in an antibody capture assay. Polyclonal antibodies W970, W954, and X179 were obtained from Dr. J. Dias at the Wadsworth Center for Laboratories and Research, New York (Liu et al., *Endocrinology* 135:682–691, 1994) where: (1) W970 was raised in rabbits immunized with peptides containing rat FSHR amino acid residues 150 to 183 coupled to KLH; (2) W954 was raised in rabbits immunized with peptides containing human FSHR amino acid residues 265 to 296; (3) X179 was similarly raised in rabbits immunized with human FSHR amino acid residues 265 to 296 and coupled at the C-terminus to ovalbumin.

For the antibody capture assay, medium binding plate (Catalogue #2586 from Costar) was coated with 5 $\mu$g/ml of PBS diluted cell lysate and left overnight at 4° C. The plate was aspirated and blocked with 5% BSA for 1 hour at 37° C. Primary antibody W970 at 1:500 dilution was added for 1 hour at 37° C. The plate was aspirated and washed with 1% BSA in PBS. Secondary goat anti-rabbit antibody conjugated with horseradish peroxidase at 1:4000 dilution was incubated for 1 hour at 37° C. The plate was aspirated and washed 3 times with 1% BSA in PBS. Hydrogen peroxidase developing solution was added and left at room temperature for 20 minutes. The plate was read at 450 nm. All three antibodies showed up to a two-fold increase in absorbance with the hFSHR366 lysate compared with that of the parental CHO-DUKX. This indicates that polyclonal antibodies W970, W955/954, and X179 can be used to detect truncated human FSHR.

The hFSHR truncated receptor was engineered to include a hexahistidyl tail (6xHis) at the carboxy terminus in order to permit affinity purification using an immobilized metal affinity column (IMAC). The column contains nickel bound through chelation with resin-bound nitrilo-tri-acetic acid (Ni-NTA). Four of the six chelation sites serve to bind the nickel to the column while leaving two sites available to chelate with the 6×His. Elution is achieved either by reducing the pH, or adding imidazole. Acid pH protonates the histidine, causing dissociation from the Ni-NTA. Imidazole competes with histidine for the Ni-NTA, again causing dissociation of the protein from the resin. The effectiveness of the washing and elution on Ni-NTA was monitored by SDS-PAGE analysis and Coomassie, silver, and immunostaining were utilized for visualization of proteins.

The results obtained from the washing and elution fractions on SDS-PAGE clearly demonstrated that Ni-NTA partially purified the soluble receptor. Negligible amounts of soluble receptor was observed in unbound, washed, or 30 mM imidazole fractions (elution of receptor is with 100 mM imidazole) by immunostaining with rabbit antibody W970 and a goat anti-rabbit horseradish peroxidase conjugate. Coomassie staining of these same fractions on SDS-PAGE gels showed many non-specific proteins being eluted with the washes. Even with removal of non-specific proteins in the wash fractions, many other contaminating proteins were still found to be present in the 100 mM imidazole elution fraction.

In addition to the Ni-NTA column, an affinity resin was prepared with immobilized FSH. The FSH was covalently bound to the CNBr resin through primary amines on the protein. In order to prevent destruction of the column by subunit dissociation under harsh washing or elution conditions, a method was developed for crosslinking the alpha and beta subunits of FSH before immobilization on the resin. Crosslinking presumably occurs between primary amines and carboxyl groups which are in close proximity, such as in the non-covalent salt bridge potentially involved in heterodimer association. The crosslinked material was then separated from both the reagents and the intermolecular crosslinked FSH by gel filtration chromatography, and the effectiveness of the crosslinking was determined by SDS-PAGE under conditions that would dissociate the non-crosslinked material. Purified crosslinked material was then anchored to CNBr resin for use in purifying the receptor.

Previously Ni-NTA enriched receptor was applied to the crosslinked-FSH affinity column to further enrich and purify the soluble hFSH receptor. The results of elution from the crosslinked-FSH affinity column indicate that contaminating proteins are still eluted with the receptor and further purification is needed to obtain a purified soluble hFSH receptor.

Example 2

Construction of the Transfer Vector for hFSHR-EC

The hFSHR cDNA, previously described as a 2.1 kb full length hFSHR construct in pUC18 in Kelton et al., *Mol. Cell. Endocrinol.* 89:141–151 (1992) was amplified by polymerase chain reaction (PCR) to generate BclI and PstI restriction sites at the 5' and 3' ends, respectively, of the portion of the hFSHR sequence coding for mature N-terminal residues 1–349 (hFSHR-EC) lacking the endogenous signal peptide and starting with Cys, and ending with $Arg_{349}$. Two oligonucleotide primers, 5'-TTTTTGATCAGTGTCATCATCGGATCTGTC-3' (SEQ ID NO: 3) and 5'-TTTCTGCAGCTATCTGAGGATGTTGTACCCC-3' (SEQ ID NO: 4), were designed to specifically amplify the DNA sequence encoding mature N-terminal amino acid residues 1–349, as well as incorporating a BclI restriction site at the 5' end and a PstI and a TAG stop codon at the 3' end of the amplified fragments.

PCR amplification was performed with these two oligonucleotide primers for 25 complete PCR cycles with each cycle involving a 30 second denaturation step at 99° C., a 30 second annealing step at 52° C, and a 1.25 minute polymerization step at 75° C.

Figure 2:
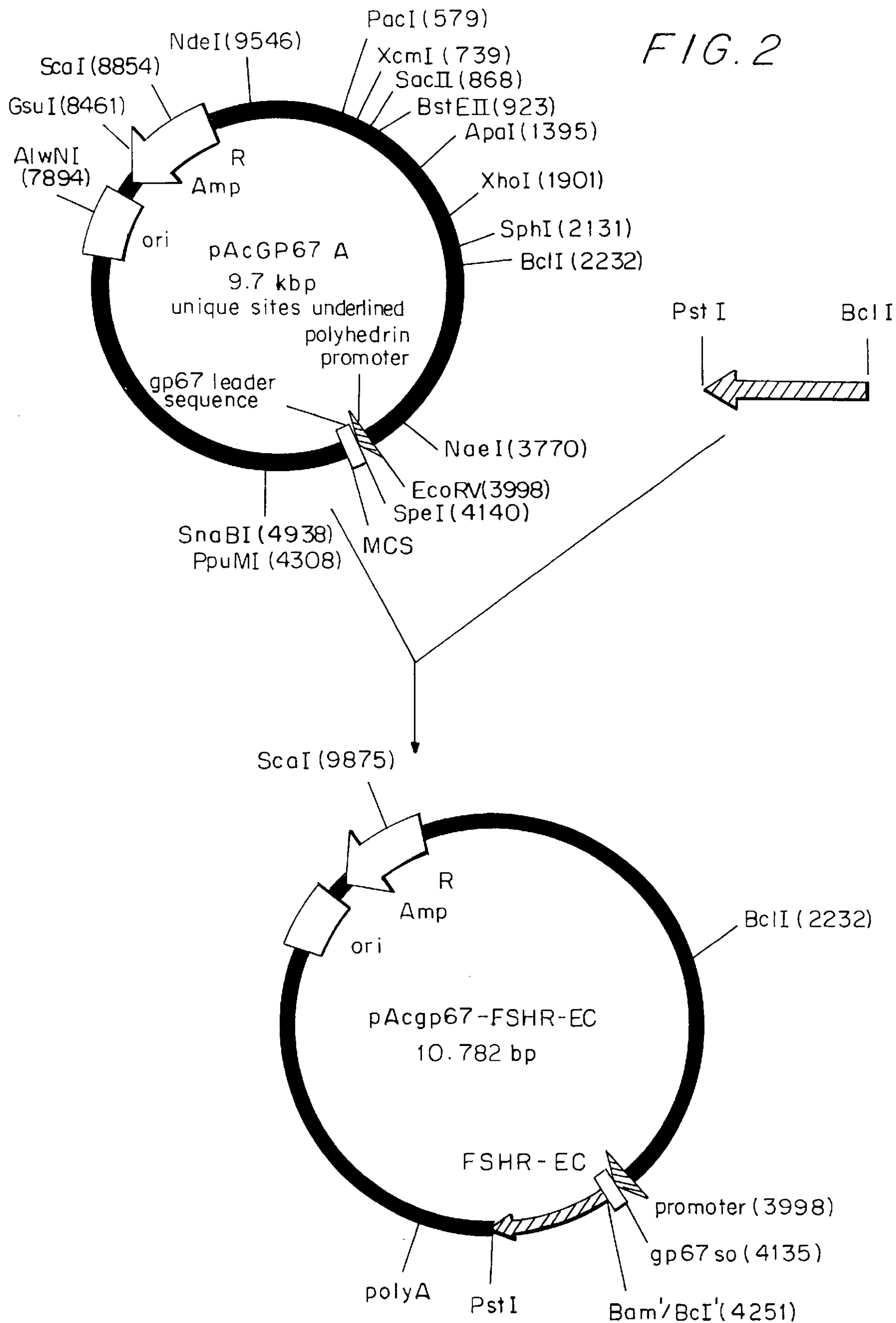
FIG. 2 shows a schematic diagram of the construction of transfer vector pAcGP67-hFSHR-EC where hatched arrow denotes the gene segment encoding the hFSHR-EC.

The fragment amplified from hFSHR cDNA was ligated into baculovirus transfer vector pAcGP67-A (Catalogue #21220P Pharmingen, San Diego, Calif.) at the BamHI and PstI cloning site within a multiple cloning site immediately 3' from and in frame with the *A. californica* glycoprotein gp67 signal sequence. The resulting transfer vector pAcGP67-hFSHR-EC also carries a strong baculovirus polyhedrin promoter, a flanking polyhedrin region from the AcNPV virus as well as an *E. coli* origin of replication and an ampicillin resistance gene for plasmid amplification and selection in *E. coli* (FIG. 2).

As cloned into pAcGP67-A, the gene fragment encoding hFSHR-EC is expressed as a gp67 signal peptide fusion protein under the control of the strong baculovirus polyhedrin promoter. This creates a fusion between the N-terminus of the mature hFSHR-EC sequence and a signal sequence for an abundantly expressed baculovirus envelope surface glycoprotein (gp67) with the gp67 signal peptide serving to direct secretion of hFSHR-EC into the culture medium. FIG. 3 shows that the ligation of the amplified fragment encoding hFSHR-EC into pAcGP67-A introduces three additional amino acid residues, Ala-Asp-Gln, between the presumed cleavage site of the gp67 signal peptide and the presumed mature hFSHR-EC open reading frame (beginning with Cys-His-His in FIG. 3). Proper vector construction was confirmed by nucleotide sequencing of the entire hFSHR-EC coding region with the constructed plasmid.

For the preparation of viral stocks, pAcGP67-FSHR-EC was transformed into *E. coli* strain MC1061, amplified and purified by well-established methods (e.g., Gruenwald et al., *Baculovirus Expression Vector System: Procedures and Methods Manual,* 2nd ed., Pharmigen, San Diego, Calif., p. 38–44, 1993; QIAPREP silica purification membranes, Qiagen, Chatsworth, Calif.). The purified transfer vector pAcGP67-hFSHR-EC was co-transfected with BACULOGOLD DNA (Catalogue #21100D Pharmigen, San Diego, Calif.) into *Spodoptera frugiperda* Sf9 cells (American Type Culture Collection, Rockville, Md.) using the calcium phosphate protocol (Gruenwald et al., supra, p. 48–52). BACULOGOLD is a modified baculovirus DNA which contains a lethal deletion and accordingly cannot encode for a viable virus by itself. When co-transfected with a complementing transfer plasmid, such as pAcGP67-hFSHR-EC, carrying the essential gene lacking in BACULOGOLD, the lethal deletion is rescued and viable virus particles can be reconstituted inside transfected insect cells.

Virus Purification, Amplification, and Verification

The virus generated in the co-transfection was plaque purified (Gruenwald et al., p. 51–52) and amplified (Gruenwald et al., p. 52–53) to generate virus particles for further infections.

The structure of the plaque purified was verified by PCR and Southern blotting. Viral DNA was prepared using virus from the second round of amplification. Cell supernatants from the amplification were filtered through a 0.2 $\mu$m filter to remove cellular debris. 10 ml of the filtered supernatant was centrifuged at 40,000 g for 30 minutes to pellet the virus. The virus pellet was resuspended in 1 ml of TE (10 mM Tris, 1 mM EDTA, pH 8.0). The resuspended virus was layered onto a 5%/50% sucrose/PBS step gradient and centrifuged at 40,000 g for 30 minutes. The purified virus, which is located between the two layers, was collected in a 1 ml volume and diluted in 3 ml of TE. The diluted virus was centrifuged at 40,000 g for 30 minutes and the viral pellet was resuspended in 200 $\mu$l of TE. The purified virus was treated with RNase A (10 $\mu$g/ml) for 30 minutes at 37° C., then 0.5% SDS and Proteinase K (10 $\mu$g/ml) were added and the mixture was incubated for an additional 30 minutes at 37° C. The mixture was phenol extracted, phenol:chloroform extracted, chloroform extracted, and ethanol precipitated. The DNA pellet was resuspended in 50 $\mu$l of TE.

1 $\mu$l of the viral DNA was used for PCR analysis using primers located 5' and 3' of the hFSHR-EC sequence. PCR was performed for 30 cycles of 1 minute at 99° C., 30 seconds at 56° C., and 1 minute at 75° C., followed by an extension step of 5 minutes at 75° C. When the PCR product was analyzed on an agarose gel, a band of the expected size was obtained. When the PCR generated DNA was digested with StuI, two bands consistent with the expected structure of the recombinant virus were obtained.

5 $\mu$g of the purified viral DNA was analyzed by Southern blot (Ausubel et al., eds., *Current Protocols in Molecular Biology*, supra). The DNA was digested with either BglII or PstI. The blots were probed with the PCR product used in construction of the transfer vector that was labeled by random oligo priming. The bands were of the expected sizes and consistent with the predicted structure of the recombinant virus.

Expression of hFSHR-EC in Insect Cells and Secretion into the Culture Media

Viral stocks prepared from co-transfection as described immediately above were used to infect HIGH-FIVE *Trichoplusia ni* insect cells (Invitrogen, San Diego, Calif.) by culturing in Grace's insect cell growth medium (Gibco BRL, Cat. # 11605-011) supplemented with 10% heat inactivated fetal bovine serum (Gibco BRL, Cat. # 16000-028, Life Technologies, Gaithersburg, Md.) for the heterologous production and secretion of hFSHR-EC. The viral titer was confirmed by end-point dilution and plaque assays following the procedures described in the Pharmingen methods manual (Gruenwald et al., supra, p. 50–52) and in O'Reilly et al., *Baculovirus Expression Vectors, A Laboratory Manual*, W. H. Freeman and Co., New York, p. 155–157, 1992, both incorporated entirely herein by reference. Infection of insect host cells in different experiments was carried out at a multiplicity of infection (MOI) of 2–10 and the media containing soluble hFSHR-EC was collected at about 96 hour post infection (see also Gruenwald et al., supra, p. 54–57).

Figure 4:
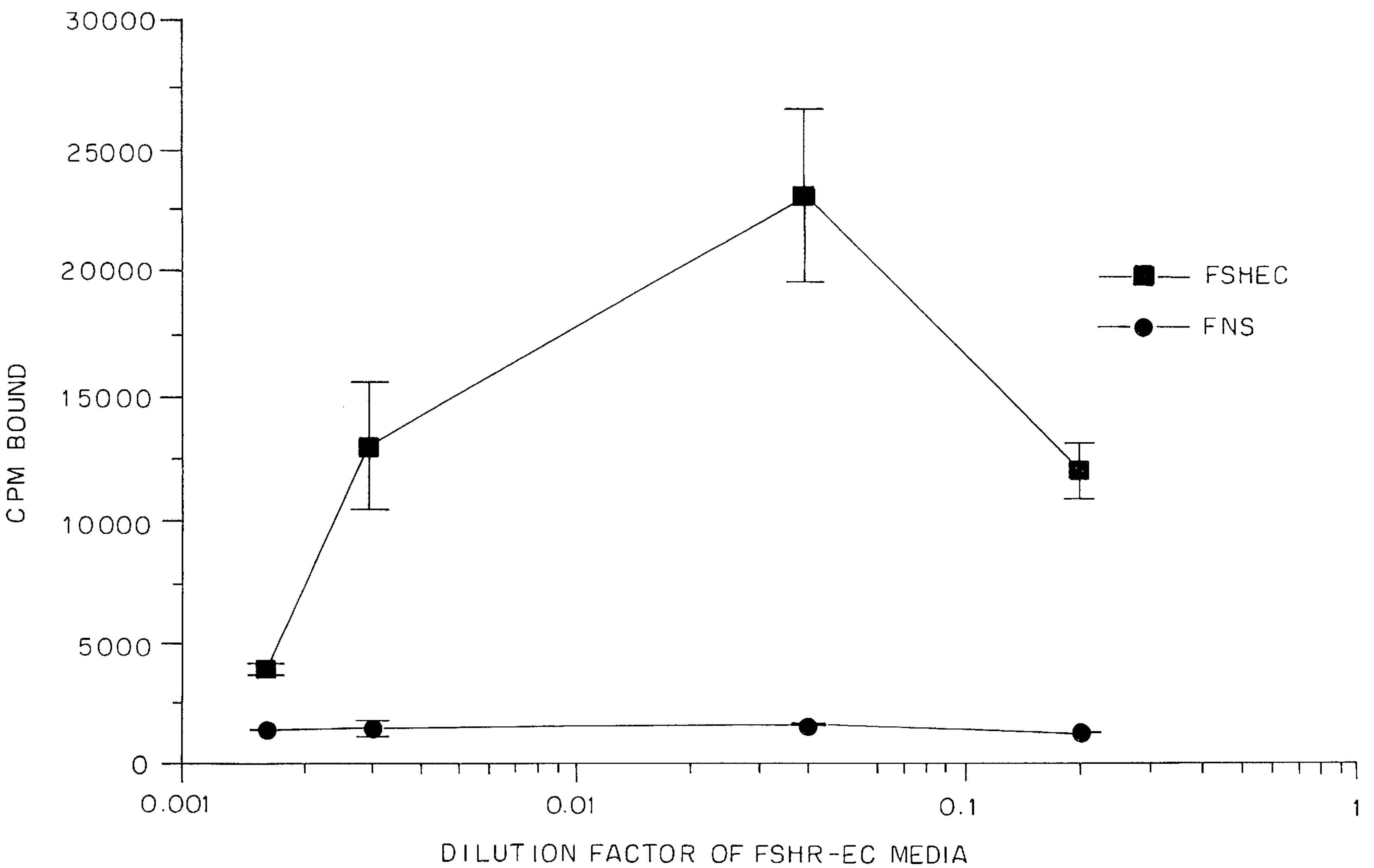
FIG. 4 shows the specific binding of soluble hFSHR-EC, secreted from insect cells into the culture medium, to $^{125}$I-hFSH. The amount of $^{125}$I-hFSH bound to insect cell-derived soluble hFSHR-EC, expressed as cpm bound, was measured with increasing media (receptor) concentrations (or increasing dilution factors) from left to right along the x-axis.

Culture media (3.5 ml) from $4\times10^6$ insect cells collected at 96 hours post-infection was serially diluted and used directly in the binding assay described for supernatants of CHO cell lysates in Example 1. The results of the binding assay are shown in FIG. 4 where it is clear that, with the exception of the most concentrated or least diluted media sample assayed (at a dilution factor of 0.2), the level of specifically bound counts increase with increasing media concentration until optimal media dilution of approximately 0.04 (25-fold dilution) is reached. A comparison of the baculovirus/insect cell system (FIG. 4) with the CHO cell system (FIG. 1 and Example 1) demonstrate the large increase in soluble hFSH receptor expression in insect cells relative to CHO cells (the sample used in the CHO cell system was obtained from $1–5\times10^7$ cells lysed into a final volume of 10 ml buffer, whereas the culture media from the insect cell system was derived from the $4\times10^6$ cells at 96 hours post infection in a media volume of 3.5 ml).

Figure 5:
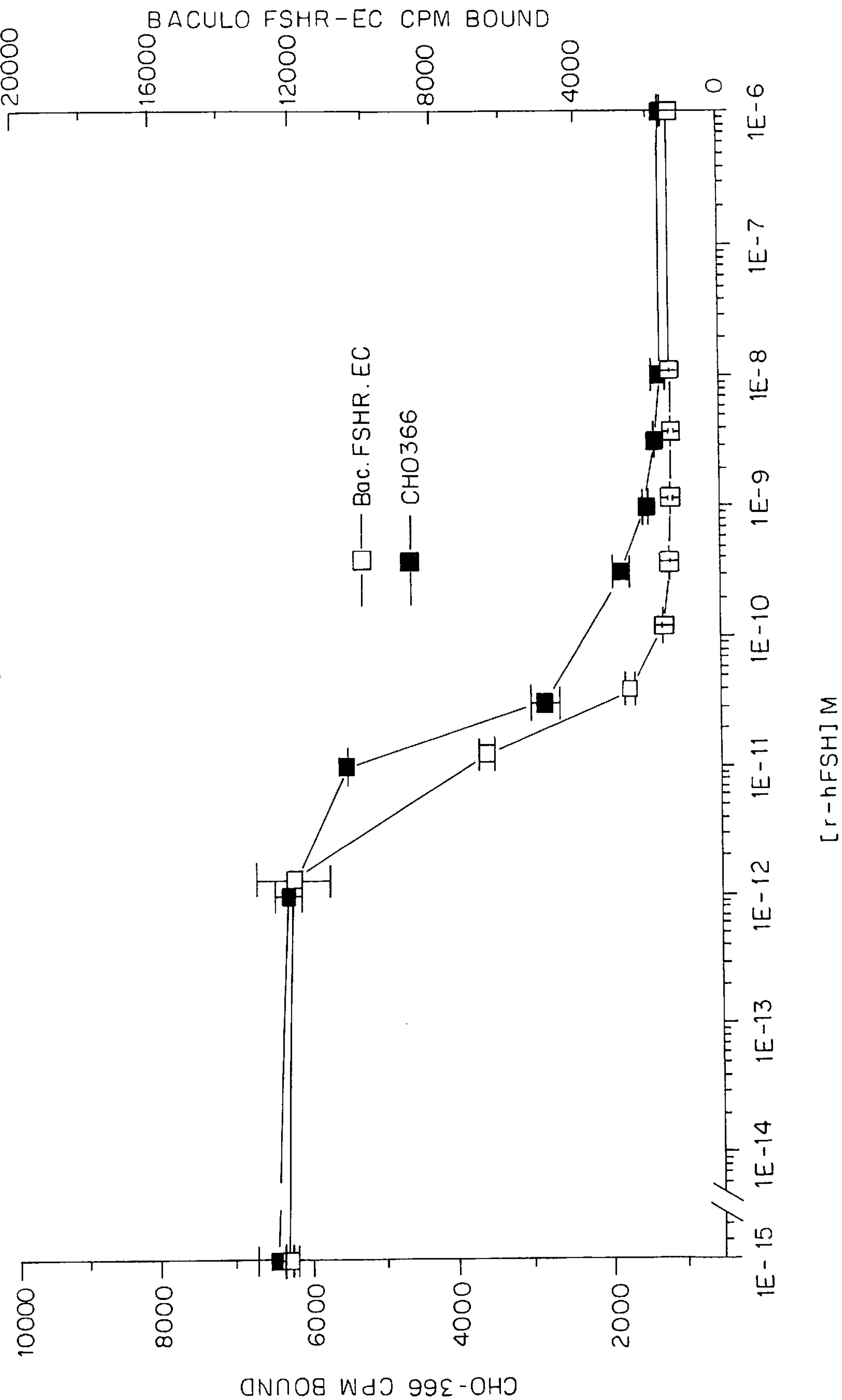
FIG. 5 shows a binding assay comparing competitive displacement of $^{125}$I -hFSH from soluble hFSHR-EC derived from both CHO cell lysates and from baculovirus/insect cell media by the presence of cold rhFSH. Increasing concentrations of non-radiolabeled rhFSH (from left to right along x-axis) compete with radiolabeled rhFSH binding to hFSHR-EC.

In a cold displacement/competitive binding assay of $^{125}$I-hFSH to soluble hFSHR-EC, a stock solution of CHO-derived FSHR-EC was made by diluting the primary stock of CHO derived-hFSHR-EC (undiluted supernatant obtained from homogenized CHO cells for binding assays in Example 1) two-fold with sucrose/Hepes/Mg/Ca buffer containing 0.1% w/v BSA (SH-BSA buffer). Another stock solution of insect cell-derived hFSHR-EC was also made by diluting the primary stock of insect cell hFSHR-EC, obtained from the culture media, 100-fold with SH-BSA buffer. Portions of these stock solutions (up to 80 $\mu$l) were combined with 10 $\mu$l (93,000 cpm, 1.1 nM) of $^{125}$I-hFSH and 10 $\mu$l of serially diluted recombinant hFSH in SH-BSA buffer and sufficient SH-BSA buffer as make-up to reach 100 $\mu$l assay volume. As shown in FIG. 5, increasing concentrations of non-radiolabeled hFSH compete with radiolabeled hFSH binding to hFSHR-EC and results in a net decrease of bound trace. It is clear the hFSHR-EC derived from both CHO and insect cell systems exhibit similar binding characteristics.

The level of hFSHR-EC expressed and secreted from insect cells was estimated to be approximately 0.2 mg/L culture media based on visualization on both silver-stained and Coomassie blue-stained SDS-PAGE gels and by calculations using observed counts of $^{125}$I-hFSH bound to soluble hFSHR-EC and the specific activity of the $^{125}$I-hFSH (ca. 130 $\mu$Ci/$\mu$g). Both CHO and insect cell-derived soluble hFSHR-EC do not require refolding in the presence of a mild denaturant, such guanidine-HCl, as the soluble hFSHR-EC expressed in both systems is fully competent in high affinity binding to hFSH.

Example 3

Scale-up of Secreted FSHR-EC Production

Production conditions of approximately 3×10$^7$ cells seeded in each T175 flask containing 35 ml of Grace's insect cell medium (Gibco BRL) supplemented with 10% heat inactivated fetal bovine serum (Gibco BRL) were used to produce secreted hFSH receptor in a 100 ml production scale-up culture of infected *Trichoplusia ni* HIGH-FIVE insect cells. Western blot and binding analysis were performed to compare media samples from the current 100 ml scale-up production with a previous smaller scale culture estimated to have ~0.2 mg/L of secreted hFSH receptor in the culture medium based on binding data (see Example 2 immediately above).

Western blot analysis of the media samples from the previous small scale batch and the current 100 ml batch showed that a comparable level of secreted hFSH receptor on a per unit volume basis was obtained for both batches.

Figure 6:
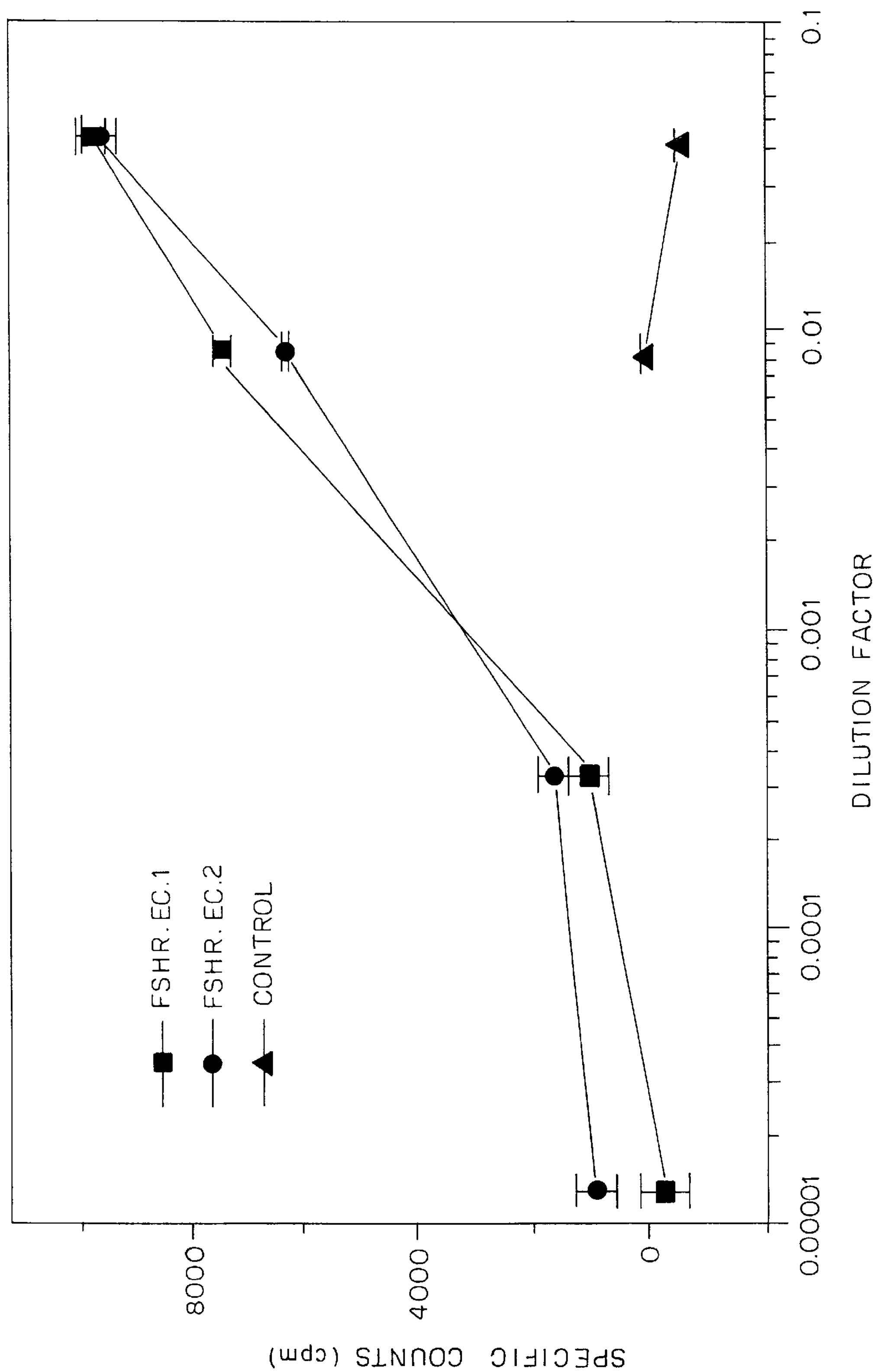
FIG. 6 shows a comparison of specific counts of $^{125}$I-FSH bound to soluble receptors produced in previous small scale batch (FSHR-EC-I) and in a 100 ml scale-up batch (FSHR-EC-II). Media from an abundantly expressed glycoprotein not related to the gonadotropin receptor generated under the same conditions as FSHR-EC in baculovirus/insect cells are shown as a negative control.

For the binding analysis (FIG. 6), media samples from either the previous batch or the new 100-ml batch were serially diluted, mixed with 300,000 cpm of $^{125}$I-hFSH (in the presence or absence of 1 $\mu$M cold FSH for non-specific and total counts, respectively), and incubated for 1 hour at 37° C. Receptor-bound trace was precipitated by the addition of polyethylene glycol. Bound counts were measured, and, as shown in FIG. 6, both sets of media samples showed similar binding capacities at each dilution, whereas media from an abundantly expressed glycoprotein not related to the gonadotropin receptor in baculovirus/insect cells (negative control) showed negligible specific binding. Therefore, by both Western blotting and binding analysis, the 100-ml batch shows comparable expression levels to those found for smaller-scale production.

Affinity Purification of Soluble FSH Receptor

Cross-linked recombinant human FSH (rhFSH) heterodimer was used as ligand in affinity purification of soluble FSH receptor because it is expected to generate a stable ligand for making affinity resin that will undergo repeated loading-elution steps without subunit dissociation. Recombinant FSH (0.33 mg/ml in 50 mM MES, pH 5.5) was crosslinked using a water soluble carbodiimide, 1-ethyl-3-(3'-dimethylaminopropylcarbodiimide, hydrochloride), abbreviated as EDAC, at a concentration of 25 mM which activates surface-exposed carboxyl groups to form an amide bond with amino groups of neighboring Lys residues. The crosslinked rhFSH was desalted on reverse-phase (Vydac C4) and analyzed by SDS-PAGE. The gel shows that crosslinking was successful since the material (crosslinked rhFSH) does not migrate at a smaller molecular weight (corresponding to separated subunits) after treatment with a reducing agent as is the case for non-crosslinked rhFSH. Approximately 8 mg of crosslinked rhFSH was generated for use in ligand affinity purification of FSHR-EC For coupling of r-hFSH to AffiGel-Hz resin (Bio Rad Laboratories, Melville, N.Y.), the kit (Cat. # 153-6060) protocol was followed by adding 3 mL of 20 $\mu$M r-hFSH in $H_2O$ to 0.3 mL of 0.117 M $NaIO_4$ combined with 0.3 mL of Bio Rad coupling buffer (final conditions: 17 mM FSH, 83 mM $NaIO_4$, pH~5.7). The oxidized r-hFSH (3 mL) was desalted using the kit desalting column (pre-equilibrated with 1× coupling buffer, pH adjusted to 5.6), giving a 2.7 mL fraction of desalted protein with an optical density (280 nm) of 0.425. Two mL of the desalted, oxidized r-hFSH was combined with 2.5 mL of the Affi-Gel resin which had been previously washed with 2×10 mL of 1× coupling buffer (pH 5.7). After rotating the suspension end-over-end for 12 hours at room temperature in a capped 15 mL conical tube, the optical density (280 nm) of the supernatant had decreased to 0.09, suggesting a coupling yield of 60–70%.

To generate a 1 mL (bed volume) column, a portion of the modified Affigel-Hz resin was added to a 0.5 cm (i.d) column. The column was washed with 20 mL of 0.1 M Hepes, 0.1 M NaCl, pH 7.0 (HB) at 1 mL/minute, with 20 mL of 0.1 M Hepes, 0.5 M NaCl, pH 7.0 at 1 mL/minute, and then with 20 mL of HB again at 1 mL/minute before loading culture media containing hFSHR-EC. Media (10 ml) from the 100-ml batch of FSR-EC was then loaded onto the column at ~0.2 ml/min at room temperature, and the loaded column was washed with 100 mM Hepes (pH 7.4)/100 mM NaCl and with 100 mM Hepes (pH 7.4)/500 mM NaCl, then eluted with 0.1 M HOAC (the washing/elution portion of the chromatogram is shown in FIG. 7). One ml fractions were collected from the elution and then analyzed by SDS-PAGE and Western blotting using polyclonal antibody X179. Successful binding/elution of the receptor was observed with the band corresponding to the soluble receptor being just visible by Coumassie staining at between 42 and 60 kDa, consistent with the MW expected for FSHR-EC. Thus, ten mls of the 100-ml batch of FSHR-EC, subjected to affinity chromatography using resin-bound rhFSH (non-crosslinked) as ligand, resulted in a visible band on SDS-PAGE (Coumassie staining) which appeared at the same position (between 42 and 60 kDa) as a band cross-reacting with anti-FSHR pAb (X179) in Western blotting.

Example 4

Demonstration of hFSH Antagonism By hFSHR-EC Using the hFSHR-Y1 in vitro Assay

To assess whether hFSHR-EC in the culture medium could antagonize hFSH action in vitro, the hFSHR-containing Y1 cell line (Y1-hFSHR) was used (Kelton et al., *Mol. Cell. Endocrin.* 89:141–151, 1992). These cells generate progesterone in response to stimulation by hFSH. The inhibitory effect of the culture medium containing hFSHR-EC on Y1-hFSHR cells stimulated by a constant dose of hFSH was determined.

The culture medium used in this experiment was prepared as follows. *Trichoplusia ni* HIGH-FIVE insect cells were seeded in T175 flasks (~2.8×10$^7$ cells per flask) containing 35 ml of Grace's insect medium (Gibco BRL, Cat. # 11605-011) supplemented with 10% heat inactivated fetal bovine serum (Gibco BRL, Cat. # 16000-028) and then infected with viral stocks of recombinant baculovirus at a multiplicity of infection of five. Protein production was allowed to continue ar 37° C. for 4 days. Cells were transferred to 50 ml conical flasks by gentle swirling and pipetting, and whole cells were pelleted by centrifugation at 1000 rpm on an H6000A rotor (ca. 200×g) for 10 minutes at 4° C. The supernatant was decanted, filtered through a 0.45 $\mu$m filter, and then centrifuged at 25,000 rpm on a Beckman L-70 ultracentrifuge for 20 minutes at 20° C. using a SW-41 swinging bucket rotor.

For the Y1-hFSHR cell assay, 96-well plates were seeded at a density of 2×10$^4$ Y1-hFSHR cells per well. The cells were grown for three days in 200 μl of $Y_1$ growth medium (Ham's F-10, Gibco BRL, Cat. # I1550-027, supplemented with 15% horse serum and 2.5% fetal calf serum) at 37° C. in a humidified atmosphere containing 5% $CO_2$. The adherent cells at 70–90% confluency were washed once with 200 μl of assay medium (Ham's F-10, 1% bovine serum albumen, 1% L-glutamine, 80 μg/ml G418), and then 100 μl fresh assay medium was added to each well followed by 100 μl aliquots of samples or standards diluted in assay medium. For the antagonism assays, a constant dose of hFSH ($3\times10^{-11}$ M), which in the absence of antagonist gives 80% of maximal stimulation, was present in each well, whereas the level of hFSHR-EC or control protein (see below) was serially diluted in assay medium. The hFSH plus hFSHR-EC mixture was either mixed at room temperature and transferred to the Y1-hFSHR cells within one hour (FIG. 8A), or it was preincubated at 37° C. for one hour before transferring it to the Y1-hFSHR cells (FIG. 8B). Alternatively, to assess the effect of culture medium on an independent pathway for adenylyl cyclase activation, a constant dose of forskolin ($1\times10^{-5}$ M) was added to each well, which stimulates high levels of progesterone production in Yl-hFSHR cells. Cells supernatants were analyzed for progesterone concentration using Serono Progesterone MAIA Clone™ immunoassay kits. The concentration of hFSHR-EC shown in the x-axis in FIGS. 8A and 8B was estimated based on $^{125}$I-hFSH binding data for the stock solution of hFSHR-EC culture medium. Using these data, the concentration of hFSHR-EC in the original culture medium was estimated to be 0.2 mg/L (4 nM, assuming a molecular weight of 50 kDa for hFSHR-EC. The original culture medium was then diluted in assay medium to give the concentration units shown in FIGS. 8A and 8B. The highest estimated concentration of hFSHR-EC tested ($8.9\times10^{-11}$) was made by diluting the original medium by a final dilution factor (in the assay well) of 0.0223.

Several control experiments were also carried out, some of which used culture medium from baculovirus/insect cells expressing a secreted glycoprotein (the control protein) other than hFSHR-EC. The cell culturing was conducted in parallel for both the hFSHR-EC and control protein expression, using the same conditions and buffers. The concentration of this control protein was not accurately determined but is probably much higher than that of hFSHR-EC. The objectives of the control experiments were to assess: i) the effect of culture medium alone on progesterone production in Y1-hFSHR cells; ii) the effect of control protein culture medium in hFSH-stimulated progesterone production in Y1-hFSHR cells; and iii) the effect of hFSHR-EC or control protein-containing baculovirus/insect cells culture media on production in Y1-hFSHR cells stimulated by a pathway independent from the gonadotropin receptor (forskolin pathway). The results of the control experiments, summarized below (averages from at least three data points, errors given as sample standard deviations), can be compared with the data shown in FIGS. 8A and 8B. First, treatment with FSHR-EC culture medium alone resulted only in basal levels of progesterone production in Y1-hFSHR cells (FSHR-EC alone at the highest concentration used, i.e., $8.9\times10^{-11}$ M or a 0.022-fold dilution of the original culture medium, gave 4.9±0.1 and 5.5±0.2 ng/ml progesterone in the non-preincubated and preincubated experiments, respectively). Further, treatment with the control protein culture medium alone (0.022-fold dilution from stock) resulted in similar basal levels of progesterone (4.7±0.2 and 5.1±0.3 ng/ml for non-preincubated and preincubated experiments, respectively). Second, the control protein culture medium (0.022-fold dilution from stock) did not antagonize progesterone in Y1-hFSHR cells stimulated by 0.03 nM r-hFSH (28.2±4.9 and 29.8±3.5 ng/ml for non-preincubated and preincubated experiments, respectively). Third, progesterone production in Y1-hFSHR cells stimulated by a constant dose (10 μM) of forskolin alone was 40.6±4.5 and 31.2±3.1 ng/ml for non-preincubated and preincubated experiments, respectively. This stimulation by 10 μM forskolin was not significantly reduced by treatment with 0.022-fold diluted FSHR-EC culture medium (37.3±6.7 and 28.3±4.0 ng/ml, for non-preincubated and preincubated experiments, respectively) or by 0.022-fold diluted control protein culture medium (44.7±3.8 and 23.0±4 ng/ml for non-preincubated and preincubated experiments, respectively).

Figure 8A:
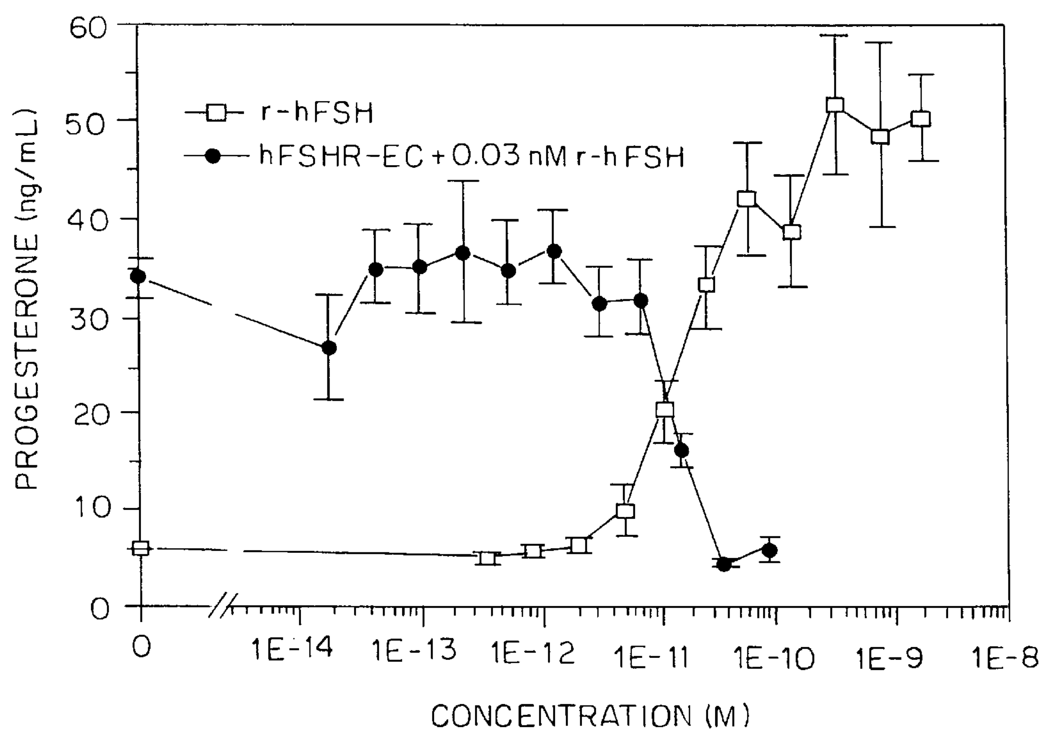
FIG. 8A shows the progesterone levels (y-axis, ng/ml) in Y1-hFSHR cell medium resulting from treatment with increasing concentration of r-hFSH (open squares) or from a constant dose of r-hFSH (0.03 nM) plus increasing concentrations of hFSH-EC from baculovirus/insect cells culture medium (closed circles). The solutions of r-hFSH and hFSHR-EC were made at room temperature and added to the Y1-hFSHR cells within one hour. The concentration units on the x-axis for r-hFSH were from amino acid analysis and for hFSHR-EC were estimates based on binding of hFSHR-EC in culture medium to $^{125}$I-hFSH of known specific activity. The highest concentration of hFSHR-EC tested in this experiment ($8.9\times10^{-11}$M) was made by diluting the original culture medium by a final dilution factor (in the assay well) of 0.0223.
Figure 8B:
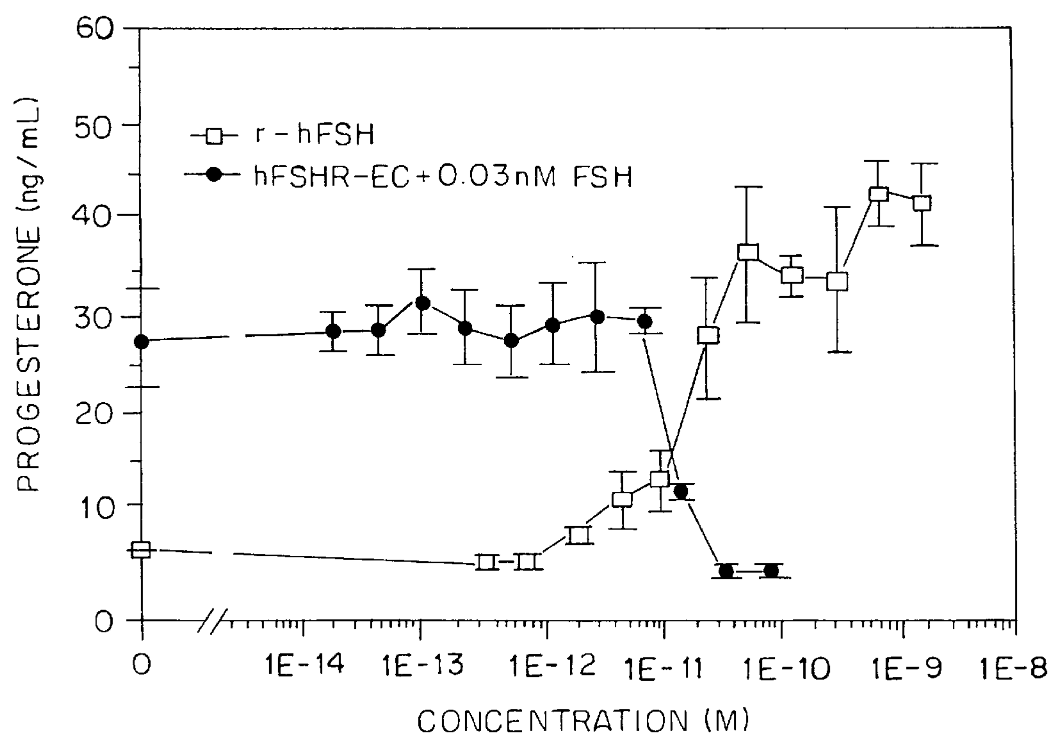
FIG. 8B shows the progesterone levels (y-axis, ng/ml) in Y1-hFSHR cell medium resulting from treatment with increasing concentration of r-hFSH (open squares) or from a constant dose of r-hFSH (0.03 nM) plus increasing concentrations of hFSH-EC from baculovirus/insect cells culture medium (closed circles). The solutions of r-hFSH and hFSHR-EC were preincubated at 37° C. for one hour and then added to the Y1-hFSHR cells. The concentration units on the x-axis are as described for FIG. 8A.

In summary, FIGS. 8A and 8B and the results described in the previous paragraph demonstrate that: i) FSH-stimulated progesterone production can be completely inhibited by hFSHR-EC in culture medium but is not affected by control culture medium; ii) FSHR-EC or control protein alone in culture medium do not stimulate progesterone production in Y1-hFSHR cells; and iii) neither hFSHR-EC nor control protein culture medium inhibit an independent pathway (forskolin stimulation) of adenylyl cyclase activation. Finally, the antagonistic effect of hFSHR-EC toward activation of hFSHR in Y-1 cells does not require extensive preincubation of hFSHR-EC with r-hFSH (compare FIGS. 8A and 8B).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

0

What is claimed is:

1. A recombinant baculovirus transfer vector, comprising a DNA segment encoding a baculovirus signal peptide joined to a DNA segment encoding an extracellular domain of a hFSH receptor, a fragment thereof, or a variant thereof where at least one amino acid of said extracellular domain is conservatively replaced with a different amino acid, which DNA segment encoding said extracellular domain or fragment or variant thereof being translationally in frame with said signal peptide and operably linked to a baculovirus promoter to form an operable linkage for expressing said extracellular domain or fragment or variant thereof in an insect host cell and secreting at least 0.2 mg/L of said extracellular domain or fragment or variant thereof into a culture medium for said insect host cell, wherein said extracellular domain or fragment or variant thereof binds the hormone ligand of said hFSH receptor.

2. A recombinant baculovirus transfer vector according to claim 1, wherein said extracellular domain of hFSHR has the amino acid sequence essentially corresponding to amino acid residues 39–390 of SEQ ID NO:2.

3. A recombinant baculovirus transfer vector according to claim 1, wherein said baculovirus signal peptide is the gp67 signal peptide of *Autographa californica*.

4. A recombinant baculovirus transfer vector according to claim 3, wherein said gp67 signal peptide has the amino acid sequence of SEQ ID NO: 5.

5. The recombinant baculovirus transfer vector according to claim 1, further comprising a Tn 7 site.

6. A method of producing secreted hFSH receptors in soluble hormone-binding form, comprising the steps of:

constructing the recombinant transfer vector of claim 5;

providing a baculovirus shuttle vector;

transforming a bacterial host cell with the recombinant transfer vector and the baculovirus shuttle vector to transpose the transposable element from the recombinant transfer vector to the baculovirus shuttle vector in said bacterial host cell;

purifying the baculovirus shuttle vector containing the transposable element;

transfecting insect cells with the baculovirus shuttle vector containing the transposable element and culturing the transfected insect cells in a culture medium to express and secrete at least 0.2 mg/L of soluble hFSH receptor; and collecting the culture medium and purifying the soluble hFSH receptor which binds a hormone ligand of said hFSH receptor.

7. A method of producing secreted hFSH receptor in soluble hormone-binding form, comprising the steps of:

constructing a recombinant transfer vector which comprises a DNA segment encoding a baculovirus signal peptide joined to a DNA segment encoding an extracellular domain of a hFSH receptor, a fragment thereof, or a variant thereof where at least one amino acid of the extracellular domain is conservatively replaced with a different amino acid, which DNA segment encoding the extracellular domain or fragment or variant thereof being translationally in frame with the signal peptide and operably linked to a baculovirus promoter for expressing and secreting the extracellular domain or fragment or variant thereof in insect cells;

co-transfecting first insect cells with the recombinant transfer vector and baculovirus DNA to generate recombinant baculovirus;

harvesting the recombinant baculovirus;

infecting second insect cells with the harvested recombinant baculovirus and culturing the infected insect cells in a culture medium to express and secrete at least 0.2 mg/L of soluble hFSH receptor; and collecting the culture medium and purifying the secreted soluble hFSH receptor which binds a hormone ligand of the hFSH receptor.

8. A method according to claim 7, wherein the second insect cells infected with recombinant baculovirus are HIGH-FIVE *Trichoplusia ni* insect cells.

9. Insect cells infected with a recombinant baculovirus containing a DNA segment encoding a baculovirus signal peptide joined to a DNA segment encoding an extracellular domain of a hFSH receptor or a fragment or a variant thereof where at least one amino acid of said extracellular domain is conservatively replaced with a different amino acid, which DNA segment encoding said extracellular domain or fragment or variant thereof being translationally in frame with the signal peptide and operably linked to a baculovirus promoter, said insect cells expressing and secreting at least 0.2 mg/L of said extracellular domain or fragment or variant thereof, wherein said expressed and secreted extracellular domain or fragment or variant thereof binds the hormone ligand of said receptor.

10. The insect cells according to claim 9, wherein said insect cells are *Trichoplusia ni* insect cells.

11. The insect cells according to claim 9, wherein said extracellular domain of hFSHR has the amino acid sequence essentially corresponding to amino acid residues 39–390 of SEQ ID NO:2.

12. The insect cells according to claim 9, wherein said baculovirus signal peptide is the gp67 signal peptide of *Autographa californica*.

13. The insect cells according to claim 12, wherein said gp67 signal peptide has the amino acid sequence of SEQ ID NO: 5.

14. A method of producing the insect cells of claim 9, comprising the steps of:

infecting insect cells with recombinant baculovirus containing a DNA segment encoding a baculovirus signal peptide joined to a DNA segment encoding an extracellular domain of a hFSH receptor or a fragment or a variant thereof where at least one amino acid of said extracellular domain is conservatively replaced with a different amino acid, which DNA segment encoding the extracellular domain or fragment or variant thereof being translationally in frame with the signal peptide and operably linked to a baculovirus promoter; and culturing the infected cells in culture medium.

* * * * *